United States Patent
Paoletti et al.

(10) Patent No.: US 8,324,202 B2
(45) Date of Patent: Dec. 4, 2012

(54) 5-PHENYL-1H-BENZO [E] [1,4] DIAZEPINE COMPOUNDS SUBSTITUTED WITH AN HYDROXAMIC ACID GROUP AS HISTONE DEACETYLASE INHIBITORS

(75) Inventors: Francesco Paoletti, Florence (IT); Maria Novella Romanelli, Calenzano (IT); Cristina Cellai, Reggello (IT); Anna Laurenzana, Tricarico (IT); Luca Guandalini, Florence (IT)

(73) Assignees: Universita Degli Studi di Firenze, Florence (IT); A.I.L. Firenze Sezione Autonoma di Firenze Dell'Associazione Italiana Contro le Leucemie, Linfomi E Mieloma—Onlus, Florence (IT)

( * ) Notice: Subject to any disclaimer, the term of this patent is extended or adjusted under 35 U.S.C. 154(b) by 0 days.

(21) Appl. No.: 12/809,958

(22) PCT Filed: Dec. 18, 2008

(86) PCT No.: PCT/IB2008/055424
§ 371 (c)(1),
(2), (4) Date: Aug. 20, 2010

(87) PCT Pub. No.: WO2009/081349
PCT Pub. Date: Jul. 2, 2009

(65) Prior Publication Data
US 2010/0331316 A1 Dec. 30, 2010

(30) Foreign Application Priority Data
Dec. 21, 2007 (IT) .................. FI2007A0288

(51) Int. Cl.
*C07D 243/24* (2006.01)
*A61K 31/5513* (2006.01)
*A61P 35/00* (2006.01)
(52) U.S. Cl. ........ 514/221; 540/509; 540/512; 540/567; 540/571; 540/575
(58) Field of Classification Search ............... 540/509, 540/512, 567, 571, 575; 514/221
See application file for complete search history.

(56) References Cited

U.S. PATENT DOCUMENTS
2008/0207590 A1* 8/2008 Deziel et al. ............ 514/211.04

FOREIGN PATENT DOCUMENTS
| WO | 02/22577 | 3/2002 |
| WO | 2007/022638 | 3/2007 |
| WO | 2008/055068 | 5/2008 |

OTHER PUBLICATIONS

Guandalini, L. "Design, synthesis and preliminary biological evaluation of new hydroxamate histone deacetylase inhibitors as potential antileukemic agents," *Bioorganic & Medicinal Chemistry Letters* vol. 18, 5071-5074 (2008).
PCT International Search Report for PCT/IB2008/055424 filed on Dec. 18, 2008 in the name of Universita' Degli Studi Di Firenze.
PCT Written Opinion for PCT/IB2008/055424 filed on Dec. 18, 2008 in the name of Universita' Degli Studi Di Firenze.
Bennett, JM et al., "Proposed Revised Criteria for the Classification of Acute Myeloid Leukemia, A Report of the French-American-British Cooperative Group," *Annals Intern Med* 103:620-625 (1985).
Finnin, MS et al., "Structures of a histone deacetylase homologue bound to the TSA and SAHA inhibitors," *Nature* 401:188-193 (1999).
Glaser, KB, "HDAC inhibitors: Clinical update and mechanism-based potential," *Biochem. Pharmacol.* 74:659-671, (2007).
Marks, PA et al., "Dimethyl sulfoxide to vorinostat: development of this histone deacetylase inhibitor as an anticancer drug," *Nature Biotechnol* 25(1):84-90, (2007).
Ryan, QC et al., "Phase I and Pharmacokinetic Study of MS-275, a Histone Deacetylase Inhibitor, in Patients With Advanced and Refractory Solid Tumors or Lymphoma," *J. Clin Oncol.* 23(17):3912-3922 (2005).
Yoshida, M et al., "Potent and Specific Inhibition of Mammalian Histone Deacetylase Both in Vivo and in Vitro by Trichostatin A," *J Biol Chem* 265(28):17174-17179 (1990).
Yoshida, M et al., "Reversible Arrest of Proliferation of Rat 3Y1 Fibroblasts in Both the G1 and G2 Phases by Trichostatin A," *Exp Cell Res* 177:122-131 (1988).
Yoshida, M et al., "Trichostatin A and trapoxin: novel chemical probes for the role of histone acetylation in chromatin structure and function," *BioEssays* 17(5):423-430 (1995).
Wang, KT et al., "Differentiation of Friend erythroleukemia cells induced by benzodiazepines," *Proc. Natl. Acad. Sci.* 81:3770-3772 (1984).
International Preliminary Report on Patentability of Jun. 22, 2010 for PCT/IB2008/055424.

* cited by examiner

*Primary Examiner* — Bruck Kifle
(74) *Attorney, Agent, or Firm* — Steinfl & Bruno, LLP

(57) ABSTRACT

Novel hydroxamate histone deacetylase inhibitors of formula (I) wherein X is C=O or $CH_2$ used as antineoplastic agent.

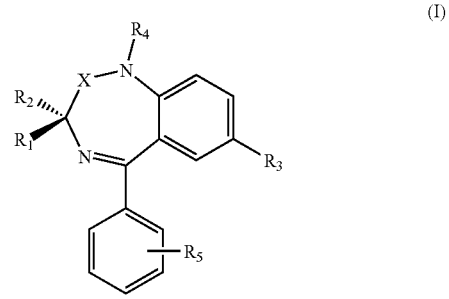

14 Claims, 2 Drawing Sheets

5-PHENYL-1H-BENZO [E] [1,4] DIAZEPINE COMPOUNDS SUBSTITUTED WITH AN HYDROXAMIC ACID GROUP AS HISTONE DEACETYLASE INHIBITORS

CROSS REFERENCE TO RELATED APPLICATIONS

The present application is the US national stage of International Application PCT/IB2008/055424 filed on Dec. 18, 2008 which, in turn, claims priority to Italian Application FI2007A000288, filed on Dec. 21, 2007.

This invention concerns novel antineoplastic agents, in particular a new class of inhibitors of the enzymatic activity of histone deacetylases (HDAC).

Several HDAC isoforms exist, classified in four distinct classes which differ for cellular localization, targeted acetylated proteins, and sensitivity to inhibitors (Mai, A et al. *Med. Res. Rev.* 2005, 25, 261).

HDACs are cellular enzymes capable of modulating gene expression and currently considered as crucial targets for the development of compounds to be employed for a pharmacological approach to cancer and termed "epigenetic therapy".

HDACs and the other enzymes involved in chromatin remodelling are important targets for anticancer therapy, as inferred by the number of inhibitors (henceforth histone deacetylase inhibitors, HDACi). Several distinct HDACi have been developed and some of them have entered clinical trials as antineoplastic agents.[1,2]

The treatment of cancers of different histogenesis with HDACi produces growth arrest, differentiation and apoptosis in tumor cells. These effects can be ascribed, at least in part, to the hyperacetylation of histone and nonhistone proteins and also to the reactivation of specific genes whose expression is responsible for the above cited cytostasis, differentiation and apoptosis in tumor cells. Preferably, such inhibition is specific, i.e., the histone deacetylase inhibitor reduces the ability of a histone deacetylase to remove an acetyl group from a histone at a concentration that is lower than the concentration of the inhibitor that is required to produce another, unrelated biological effect. Conversely, normal cells showed to be much less sensitive to HDACi and did not produce appreciable untoward effects.

A well known class of HDACi is that belonging to the family of trichostatin-A (TSA,) a hydroxamic acid derivative isolated from *Streptomyces hygroscopicus*, which has been shown to inhibit histone deacetylase activity and arrest cell cycle progression in cells in the G1 and G2 phases (Yoshida et al , J Biol Chem 265 17174-17179, 1990, Yoshida et al, Exp Cell Res 177 122-131, 1988): the hydroxamic group is functional for activity since it coordinates the $Zn^{2+}$ cation located in the active site of HDACs at the bottom of the pocket for the N-acetylate residue of lysine (Yoshida, M et al. Bioessays 1995, 17, 423).

Other hydroxamic acid derivatives were independently developed, including SAHA (suberoyl anilide hydroxamic acid or Vorinostat), recently approved by the FDA for the treatment of cutaneous T-cell lymphoma (Marks, P. A.; Breslow, R. Nature Biotechnol. 2007, 25, 84).

Finnin, M. S. et al. Nature 1999, 401, 188, teaches that TSA and SAHA inhibit cell growth, induce terminal maturation, and prevent the formation of tumors in mice.

Other either natural or synthetic non-hydroxamate HDACi have also been developed and entered clinical trials (Glaser, K. B. Biochem. Pharmacol. 2007, 74, 659).

However, despite the high efficacy of hydroxamic-based HDACi in vitro, their use in the clinic may be limited due to the fact that relatively high concentrations are required for chelating the $Zn^{2+}$ cation and producing, eventually, a therapeutic effect in vivo. Relatively high doses of HDACi can be toxic and cause serious inconvenience to the host.

Other known HDACi of great clinical interest for the treatment of different types of cancers were for instance the compound MS-275, a benzamidic derivative described in *J. Clin. Oncol.* 2005; 23:3912-22 and FK228 depsipeptide, a natural cyclic polypeptide that was isolated from dal *Chromobacterium violaceum*.

Again, a problem with these HDACi is their potential toxicity when administered at high concentrations in vivo, and this toxicity limits their use only to patients who did not respond to conventional anticancer therapy or were relapsed after treatment with cytotoxics.

Furthermore, it was known, since many years, that some benzodiazepines possess differentiative properties and can induce terminal maturation in murine erythroleukemia cells of Friend (see "*Differentiation of Friend erythroleukemia cells induced by benzodiazepines*" Proc. Natl. Acad. Sci. USA, 1984; 81: 3770-2)

WO-A-2007022638 discloses a large panel of compounds exhibiting HDACi activity and some of them were containing a benzodiazepine nucleus (serving as the cap) with a carbonilic group at position 5.

The object of the invention is therefore to provide new antineoplastic agents capable of inhibiting HDACs, having a low toxicity profile as compared to other known HDACi and high efficacy in modulating the expression of key genes involved in tumorigenesis.

The above object is achieved with some new compounds comprising a hydroxamic function capable of chelating the $Zn^{2+}$ that is located in the catalytic site of HDACs, conjugated with.a benzodiazepine mojety.

The novel hybrids compounds act as powerful HDACi with an activity comparable to that of other known inhibitors such as the well known compound SAHA as regards the ability to induce growth arrest, differentiation and apoptosis in cancer cells, while they present low toxicity against normal cells in vitro.

Furthermore, the compounds according to the present invention have shown to act in synergy with some conventional antineoplastic agents so as to decrease their concentrations and enhance their therapeutic efficacy.

In another aspect, the invention provides HDACi which are active toward a wide spectrum of the different classes of HDACs, enhance the expression of a panel of genes and induce hyperacetylation of histone and nonhistone proteins that control several cellular function, including cell proliferation, repair of DNA damages and the activation of programmed cell death.

According to a further aspect, the invention relates to a composition comprising at least a compound of general formula (I) and a pharmaceutically acceptable excipient. According to a further aspect, the invention relates to the use of a compound with a general formula as in (I) for the preparation of an antineoplastic agent.

Further aspects and features of the invention will be apparent to experts in this field from the following detailed, non-limiting description with reference to the attached drawings in which.

Figure 1:
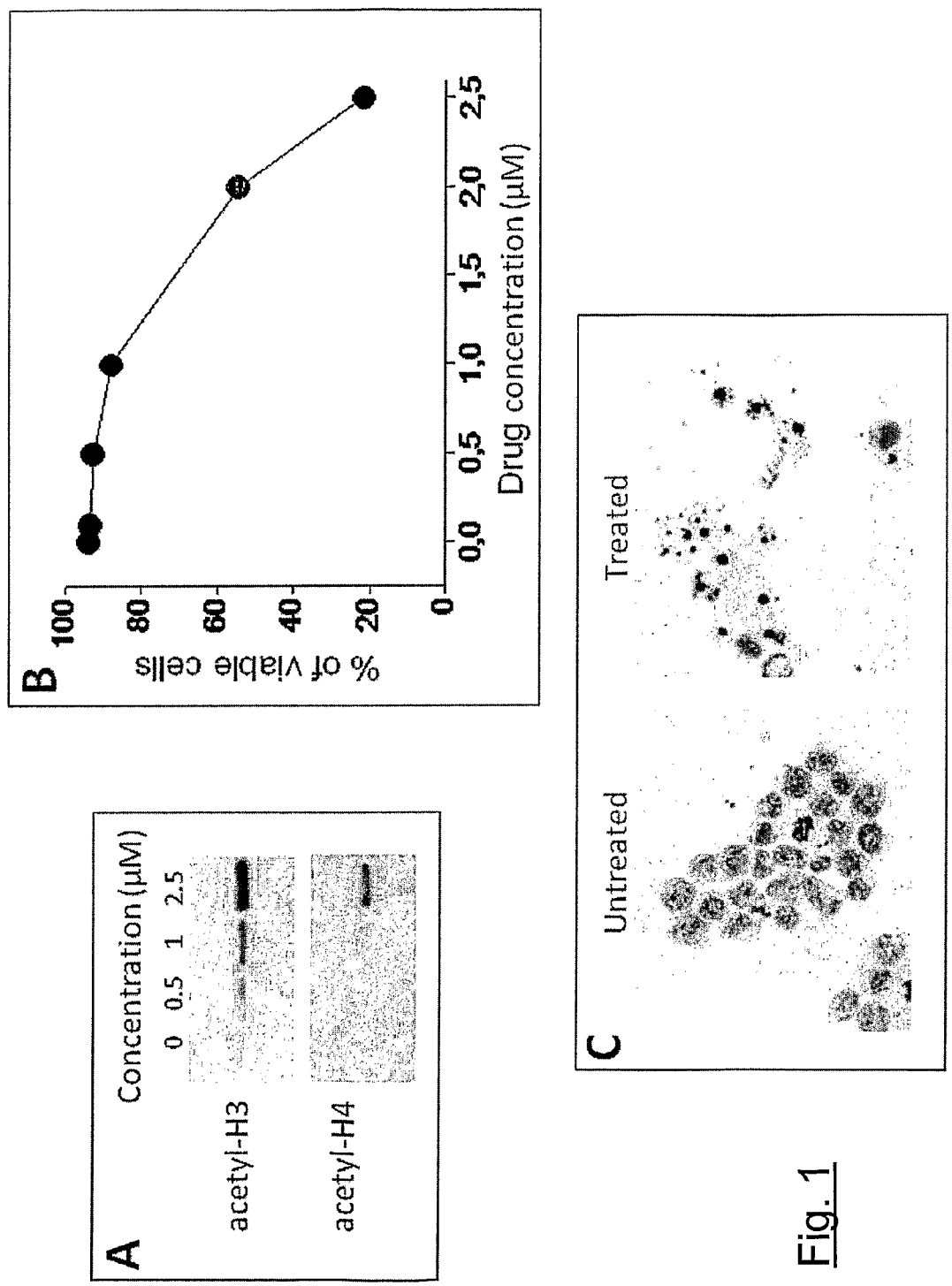
FIG. 1 shows the biological effects of a compound comprised within the general formula (I) according to the present invention on the human acute promyelocytic leukemia cells NB4.

The compounds developed according to the present invention have all the general formula (I)

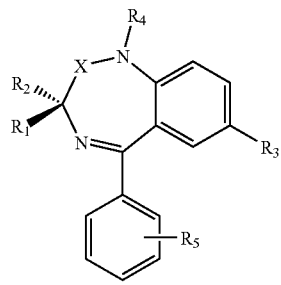

wherein X is C=O or CH$_2$;

R$_1$, R$_2$, R$_3$, R$_4$ e R$_5$ are independently hydrogen or (C$_1$-C$_4$) alkyl, halogen, NO$_2$, alkoxy, alkylthio, amino, dialkylamino or A-CONHOH, wherein the alkyl or alkoxy group can be for example methyl, ethyl, n-propyl, iso-propyl, n-butyl, iso-butyl, tert-butyl;

wherein A is selected from (C$_1$-C$_8$) alkyl, (C$_2$-C$_8$) alkenyl, (C$_2$-C$_8$) alkynyl, (C$_1$-C$_8$) alkyl-NHCH$_2$, (C$_2$-C$_8$)alkenyl-NH—CH$_2$, —(C$_0$-C$_8$)alkyl-Y—(C$_1$-C$_8$)alkyl, for example methyl, ethyl, n-propyl, iso-propyl, n-butyl, iso-butyl, tert-butyl, pentyl, hexyl, heptyl, octyl, each one saturated or unsaturated with one or more than one double or triple bonds, wherein Y is —NHCO—, —O—, —NH—, —S; when al least one among R$_1$, R$_2$, R$_3$, R$_4$ and R$_5$ is A-CONHOH.

According to the present invention, at least one of R$_1$ and R$_2$ is preferably hydrogen. In case R$_1$ and R$_2$ are different, the compound will be in racemic form, or in stereoisomerically pure form (R) or (S) or in non-racemic (R)+(S) mixtures.

Specific compounds according to the present invention are:
N1-hydroxy-N8-(1-methyl-2-oxo-5-phenyl-2,3-dihydro-1H-benzo[e][1,4]diazepin-3-yl)octanediamide;
N1-(7-chloro-1-methyl-2-oxo-5-phenyl-2,3-dihydro-1H-benzo[e][1,4]diazepin-3-yl)-N8-hydroxyoctanediamide;
N1-hydroxy-N7-(1-methyl-2-oxo-5-phenyl-2,3-dihydro-1H-benzo[e][1,4]diazepin-3-yl)heptanediamide;
N1-hydroxy-N8-(1-methyl-2-oxo-5-phenyl-2,3-dihydro-7-nitro-1H-benzo[e][1,4]diazepin-3-yl)octanediamide;
N1-(7-chloro-5-(2-fluorophenyl)-2-oxo-2,3-dihydro-1H-benzo[e][1,4]diazepin-3-il)—N8-hydroxyoctanediamide;
N1-hydroxy-N8-(1,3-dimethyl-2-oxo-5-phenyl-2,3-dihydro-1H-1,4-benzo[e][1,4]diazepin-7-yl)octanediamide;
N1-hydroxy-N8-(1,3-dimethyl-2-oxo-5-phenyl-2,3-dihydro-1H-1,4-benzo[e][1,4]diazepin-7-yl)-heptanediamide;
N1-hydroxy-N8-(1-methyl-2-oxo-3-ethyl-5-phenyl-2,3-dihydro-1H-1,4-benzo[e][1,4]diazepin-7-yl)-octanediamide;
N1-hydroxy-N8-(1-methyl-2-oxo-5-phenyl-2,3-dihydro-1H-1,4-benzo[e][1,4]diazepin-7-yl)-octanediamide;
N1-hydroxy-N8-[1-methyl-2-oxo-5-(2-fluorophenyl)-2,3-dihydro-1H-benzo[e][1,4]diazepin-7-yl]-octanediamide;
N1-hydroxy-N8-[1-methyl-2-oxo-5-(2-fluorophenyl)-2,3-dihydro-1H-benzo[e][1,4]diazepin-7-yl)-octanediamide;
N-hydroxy-8-(5-phenyl-2,3-dihydro-benzo[e][1,4]diazepin-1-yl)-8-oxo-octanamide;
N-hydroxy-8-(5-phenyl-7-nitro-2,3-dihydro-benzo[e][1,4]diazepin-1-yl)-8-oxo-octanamide;
N-hydroxy-6-(1,3-dimethyl-2-oxo-5-phenyl-2,3-dihydro-1H-benzo[e][1,4]diazepin-7-yl)-5-hexynamide;
N-hydroxy-7-(1,3-dimethyl-2-oxo-5-phenyl-2,3-dihydro-1H-benzo[e][1,4]diazepin-7-yl)-6-heptynamide;
N-hydroxy-6-(1-methyl-2-oxo-5-phenyl-2,3-dihydro-1H-benzo[e][1,4]diazepin-7-yl)-5-hexynamide;
N-hydroxy-6-[4-(1-methyl-2-oxo-2,3-dihydro-1H-benzo[e][1,4]diazepin-5-yl)-phenyl]-5-hexynamide;
N1-hydroxy-N8-[4-(1-methyl-2-oxo-2,3-dihydro-1H-benzo[e][1,4]diazepin-5-yl)-phenyl]-octanediamide;
N-hydroxy-5-(1-methyl-2-oxo-5-phenyl-2,3-dihydro-1H-benzo[e][1,4]diazepin-7-yl)-4-pentynamide;
N-hydroxy-7-(1-methyl-2-oxo-5-phenyl-2,3-dihydro-1H-benzo[e][1,4]diazepin-7-yl)-6-heptynamide;
N1-hydroxy-N6-(1-methyl-2-oxo-5-phenyl-2,3-dihydro-1H-benzo[e][1,4]diazepin-3-yl)hexanediamide;
N1-hydroxy-N9-(1-methyl-2-oxo-5-phenyl-2,3-dihydro-1H-benzo[e][1,4]diazepin-3-yl)nonanediamide.

In a preferred embodiment, the invention relates to compounds of formula (II):

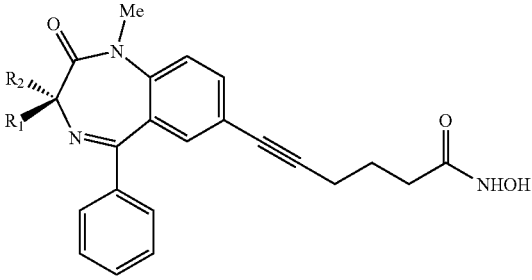

wherein R$_1$, R$_2$ independently are hydrogen or methyl.

From the in vivo tests, described in details afterwards with reference to the figures, compound (II), where only one of the R$_1$ and R$_2$ substituents is a methyl group and the other one is hydrogen, is particularly effective in inhibiting HDAC, therefore facilitating, in its enantiomerically pure (S) form, H4 histone acetylation, and it shows good activity to induce H3 histone acetylation in a dose-dependent way. On the contrary, the (R) form does not show hyperacetylating activity on H4 histones, but it maintains a good activity toward H3 histone.

The same compound, particularly in its racemic form, shows a good ability to induce apoptosis, blocking the growth of leukemic cells.

Compound (II) where both R$_1$ and R$_2$ are hydrogen, shows an excellent apoptotic activity, together with a good H4 histone acetylating activity.

In another preferred embodiment, the invention includes compounds having the following formula (III),

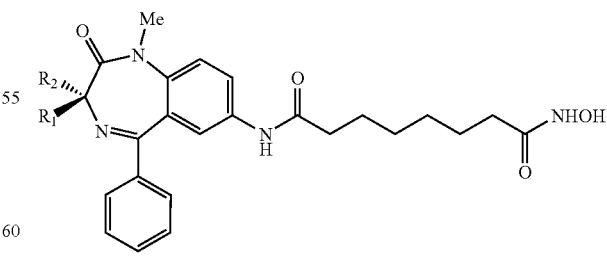

wherein R$_1$, R$_2$ independently are hydrogen or methyl.

Also in this case, the preferred compounds with formula (III) are those in which one between R$_1$ and R$_2$ substituents is methyl and the other is hydrogen. In vitro tests have shown that the enantiomerically pure (R) form is endowed with excellent H4 histone acetylating activity and good H3 histone acetylating activity, in addition to a high apoptotic activity. Also the racemate and the (S) form show good inhibitory activity.

Also compound (III) where both $R_1$ and $R_2$ are hydrogen atoms shows good acetylating and apoptotic activities.

Other preferred compounds are substances where the A-CONHOH chain is placed in the 3 position of the benzodiazepine ring, being one of residues $R_1$ or $R_2$.

Among these, a preferred compound according to the invention is shown in the following formula (IV):

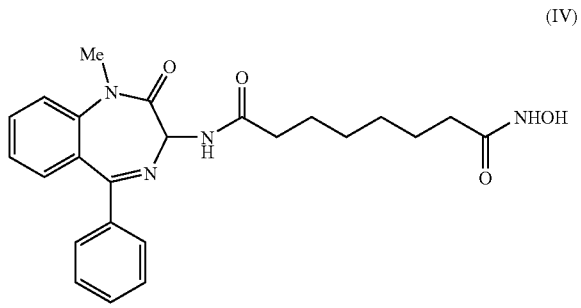

(IV)

Also this compound showed good acetylating activity of H4 histone and reasonably good activity toward H3 histone in the biological tests.

The compounds of the invention may be in the anhydrous or hydrated forms, may be as non-salified molecules or as salts obtained through protonation of the imminic function with a suitable acid, for instance as chloride, bromide, iodide, sulphate, phosphate or carboxylate salt. The compounds of the invention can be administered as salts obtained through deprotonation of the hydroxamate function with a suitable base (for instance sodium hydroxide or another strong base).

In another aspect, the present invention provides pharmaceutically acceptable compositions including a compound of formula (I) optionally as association with other medications, preferably chemioterapics, formulated together with one or more pharmaceutically acceptable carriers (additives) and/or diluents, allowing oral or parenteral administration. The additives and/or diluents can be solid, liquid and semisolid.

Solid additives can be, with no limitation, starch, cellulose, talc, glucose, lactose, sucrose, gelatin, malt, rice, flour, silica gel, magnesium stearate, sodium stearate, glycerin monostearate, sodium chloride, powdered milk and similar substances employed in pharmaceutical formulations. Liquid and semisolid additives can be, with no limitation, glycerin, propylene glycol, water, ethanol and animal or vegetal oils. Liquid carriers, particularly suitable for parenteral administration, include water, saline solution, aqueous solution of dextrose and glycols.

A compound with formula (I) can be administered at a dosage level which depends on a variety of factors including the kind and the severity of the pathology, the age and the general health of the patient, the potency of the compound, the administration route and the kind of pharmaceutical formulation. Preferred administration routes are the parenteral administration, for instance the intravenous infusion, and oral administration, for instance capsules, tablets, solutions. Daily effective dosages include dosages from 10 to 1000 mg, preferably from 50 to 500 mg or from 100 to 200 mg daily. Administration regimens include, for instance, intravenous infusion of 100 ml (from 0.1 to 10 mg/mL) of compound for an adequate term, for instance two hours. The treatment can be continued daily for several consecutive days, or alternated, for instance once, twice or three times a week, or daily for one, two or more weeks, alternated with a week of pause.

Oral administration includes equivalent administration regimens and dosages. For example, a mean daily dose of about 50 to 500 mg of drug, or in alternated or consecutive days during a week of treatment, and for an overall period of 4 or more weeks.

According to the invention, compounds of formula (II) and (III) can be prepared starting from 2-amino-5-nitrobenzophenone as described in scheme 1. $R_1$ and $R_2$ can be, for example and with no restriction for the invention, independently hydrogen or a methyl group.

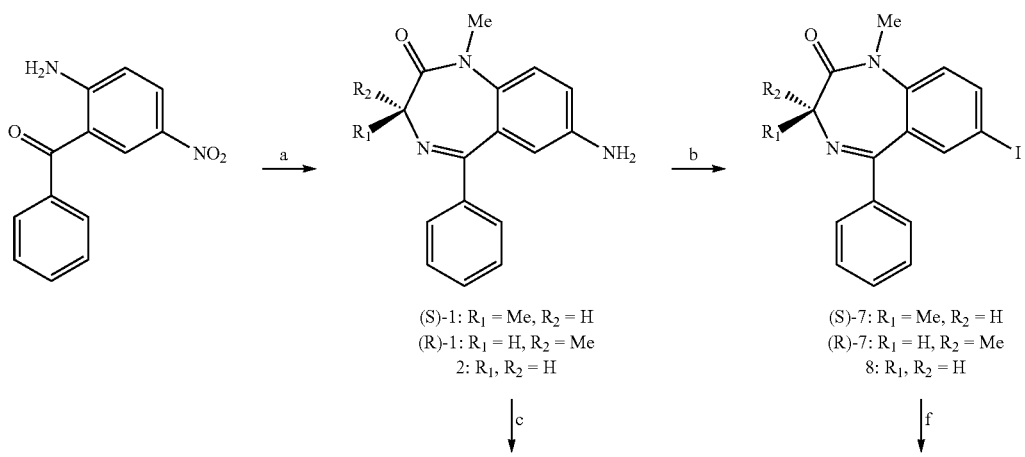

-continued

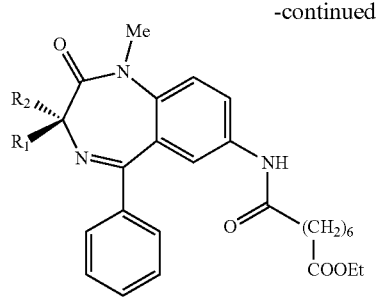

(S)-3: R$_1$ = Me, R$_2$ = H
(R)-3: R$_1$ = H, R$_2$ = Me
4: R$_1$, R$_2$ = H

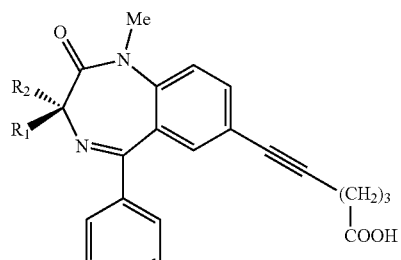

(S)-9: R$_1$ = Me, R$_2$ = H
(R)-9: R$_1$ = H, R$_2$ = Me
10: R$_1$, R$_2$ = H

↓ d,e

↓ e

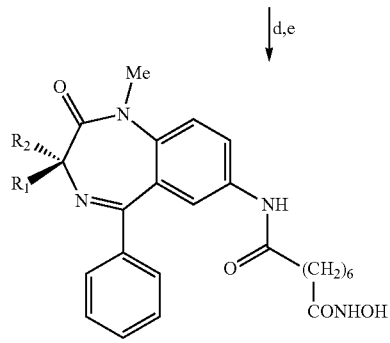

(S)-5: R$_1$ = Me, R$_2$ = H
(R)-5: R$_1$ = H, R$_2$ = Me
6: R$_1$, R$_2$ = H

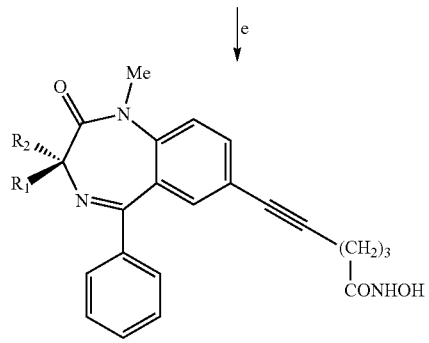

(S)-11: R$_1$ = Me, R$_2$ = H
(R)-11: R$_1$ = H, R$_2$ = Me
12: R$_1$, R$_2$ = H

In particular, in step a) of the process, in order to obtain the diazepine ring and to reduce the nitro group, 2-amino-5-nitrobenzophenone is reacted with:

i) (S) or (R)-Fmoc-alanine, or Fmoc-glicine, and SOCl$_2$;
ii) Et$_3$N, CH$_2$Cl$_2$;
iii) Me$_2$SO$_4$, MeONa;
iv) SnCl$_2$2H$_2$O, HCl.

For the preparation of compounds of formula (II), in step b) of the process the amine group is replaced with iodine by reaction with NaNO$_2$ and KI; in step f) iodine is replaced with the proper chain by reaction with 5-hexynoic acid, CuI, Pd(PPh$_3$)$_4$, Et$_3$N; finally, in step e) the hydroxamate function is introduced by reaction with: i) TBDMSONH$_2$, BOP—Cl; ii) MeOH.

For the preparation of compounds of formula (III), after step a) the following steps are performed:

c) reaction with ethyl hydrogensuberate, N-(3-dimethylaminopropyl)-N'-ethyl carbodiimide HCl (WSC HCl), 1-hydroxybenzotriazole (HOBT);
d) NaOH; and
e): i) TBDMSONH$_2$, BOP—Cl; ii) MeOH.

According to the present invention, for the preparation of compound of formula (IV) different synthetic strategies are possible, as shown in scheme 2.

Scheme 2

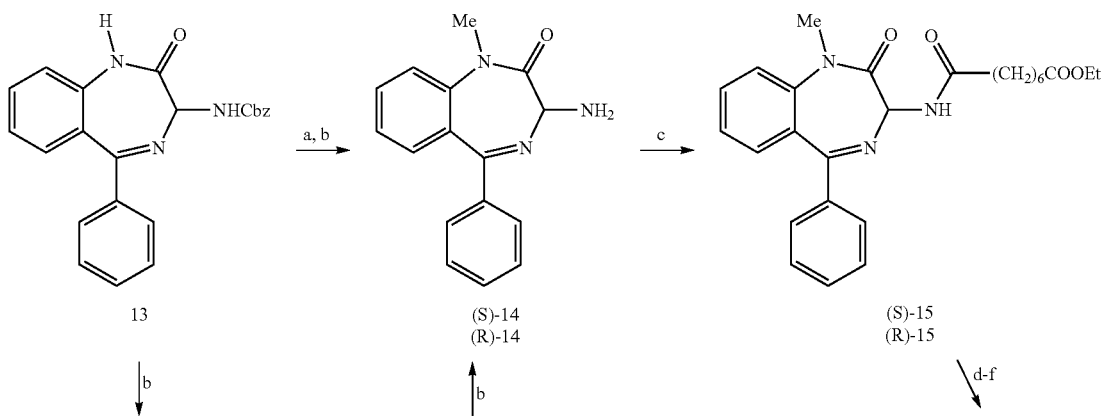

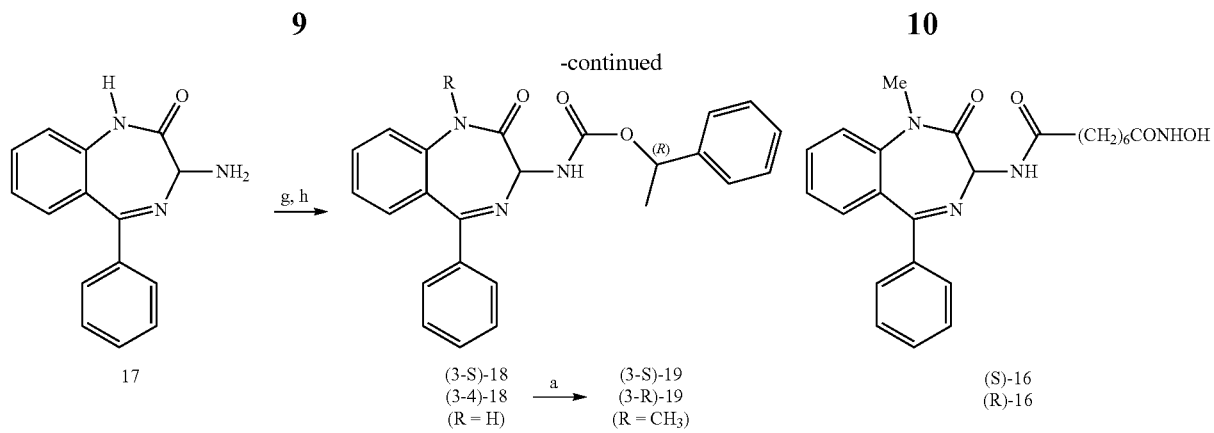

Benzyl (2-oxo-5-phenyl-2,3-dihydro-1H-benzo[e][1,4]diazepin-3-yl)carbamate is reacted with a) NaH, CH$_3$I; b) 33% HBr/AcOH; obtaining 3-amino-1-methyl-5-phenyl-1H-benzo[e][1,4]diazepin-2(3H)-one as a racemate. The following steps are then performed: c) reaction with ethyl hydrogen suberate, WSC, HOBT; d) reaction with NaOH; e) reaction with H$_2$NOSiMe$_2$tBu, BOP—Cl, Et$_3$N; and f) with MeOH; obtaining product of formula (IV).

Alternatively, 3-amino-1-methyl-5-phenyl-1H-benzo[e][1,4]diazepin-2(3H)-one can be prepared in enantiomerically pure (R) or (S) forms reacting benzyl (2-oxo-5-phenyl-2,3-dihydro-1H-benzo[e][1,4]diazepin-3-yl)carbamate with b) 33% HBr/AcOH; then g) 4-nitrophenyl (R)-1-phenylethyl carbonate; and finally separating the two diastereoisomers by chromatography in step h).

In this case, performing the already mentioned steps c-f), final product (IV) is obtained in enantiomerically pure form with respect with the stereocenter C-3.

Applications

Like other structurally different HDACi, the compounds of the invention are capable of modifying chromatin assembly and producing therefore epigenetic effects.

These agents can be employed as modulators of gene expression and represent an useful tool to interfere significantly with several cellular functions at different levels including molecular, biochemical and morphologic aspects. These compounds can be used as more or less specific inhibitors of different classes of HDACs, enhance the expression of a restricted, yet crucial, panel of genes and lead to the hyperacetylation of both histone and nonhistone proteins playing a pivotal role in the control of cell proliferation, apoptosis, DNA repair and tumorigenesis.

As reported for other known HDACi, compounds of the invention can be usefully applied in the field of experimental and clinical oncology. They behave as powerful anticancer agents with high efficacy towards both hematologic and solid malignancies. They also act as cytostatic agents and can restore the mechanisms that control the differentiation and apoptosis, which processes are often blocked or severely altered in cancer cells.

These HDACi can be used alone or in combination with agents currently used in conventional chemotherapy so as to decrease drug concentrations and obtain a significant therapeutic efficacy at low doses that do not produce untoward effects to the host. For instance, several compounds of the invention showed to act in synergy with ATRA (all-trans-retinoc acid) and were capable of markedly increasing its potency in promoting granulocyte-like differentiation in human acute promyelocytic leukemia cells NB4. It must be stated again that tumor cells are much more sensitive to HDACi than normal cells.

The benzodiazepine-hydroxamate hybrids in addition to the reported HDAC-inhibitory activity might also display anti-anxiolytic, anti-convulsant, myorelaxant, anti-inflammatory effects. Recent data describe that HDACi play an important role as modulators of production of chemical mediators in inflammation and activity of growth factors, and might be helpful for the treatment of patients with thalassemia.

Other applications of benzodiazepine-hydroxamate hybrids are involved in the control of angiogenesis, of the metastatic process as well as in the development and progression of neurodegenerative diseases.

The invention will be explained in more details by means of the following, non-limiting examples.

All melting points were taken on a Büchi apparatus. $^1$H-NMR, $^{13}$C-NMR, HSQC and COSY spectra were recordered on a Bruker Avance 400 spectrometer. Infrared spectra were recorded with a Perkin-Elmer 681 spectrofotometer in Nujol mull for solids and neat for liquids. Thin layer chromatography (TLC) was performed on Kieselgel Merck F254 silica gel plates and on F254 neutral alumina plates. Chromatographic separations were performed on a silica gel column by gravity chromatography (Kieselgel 40, 0.063-0.200 mm; Merck) or flash cromatography (0.040-0.063 mm; Merck) using the proper eluents. Optical rotation was measured at a concentration of 1g/100 mL (c=1) with a Perkin-Elmer polarimeter (accuracy 0.002°). GC-MS analysis were performed on a Perkin-Elmer Turbomass-Autosystem XL. Alternatively, mass spectra were recordered on a Linear Ion Trap (LTQ)-Thermo-Finnigam spectrometer. Compounds were named following IUPAC rules as applied by Beilstein-Institute AutoNom (version 2.1) software for systematic names in organic chemistry.

Example 1

Synthesis of (S)-7-amino-1,3-dimethyl-5-phenyl-1H-benzo[e][1,4]diazepin-2(3H)-one [(S)-1]

Commercially-available (S)-Fmoc-alanine (2.98 g, 0.96 mmol) was suspended in ethanol-free CHCl$_3$ (30 mL) and SOCl$_2$ (7 mL) was added under N$_2$. The mixture was heated at 50° C. for 1 h, then the solvent was removed under vacuum, the residue was dissolved into CHCl$_3$ (30 mL), commercially-available 2-amino-5-nitro-benzophenone (2.32 g, 0.96 mmol) was added, and the mixture was heated for 2 h at 60° C. After cooling, a saturated solution of NaHCO$_3$ was added, the organic phase was collected and dried ($Na_2SO_4$), then the solvent was removed under vacuum obtaining (9H-fluoren-9-yl)methyl 1-(2-benzoyl-4-nitrophenylamino)-1-oxopropan-2-ylcarbamate (98% yield). This compound was dissolved in $CH_2Cl_2$ (40 mL), $Et_3N$ (10 mL) was added and the mixture was heated at 40° C. for 30 h under $N_2$. The solvent was removed under vacuum and the residue was partitioned between 2N HCl and ethyl acetate; the aqueous layer was made alkaline with 10% NaOH and extracted with $CH_2Cl_2$. After drying ($Na_2SO_4$) and removal of solvent, the residue was purified by flash chromatography (cyclohexane/ethyl acetate 6:4 as eluent) yielding (S)-3-methyl-7-nitro-5-phenyl-1H-benzo[e][1,4]diazepin-2(3H)-one in 25% yield.

[$^1H$]-NMR ($CDCl_3$): 1.77 (d, 3H, J=6.4 Hz, $CH_3$); 3.78 (q, 1H, 6.4 Hz, CHCO); 7.39-7.43 (m, 3H, aromatic protons); 7.74-7.49 (m, 3H, aromatic protons); 8.24 (d, 1H, J=2.4 Hz, H-6); 8.38 (dd, 1H, J=8.8 Hz, 2.4 Hz, H-8); 10.25 (s, br, 1H, NH) ppm.

The obtained compound (0.53 g, 1.80 mmol) was added to a solution of MeONa (0.04 g, 1 eq) in anhydrous DMF (5 mL) and stirred at room temperature for 1 h, then dimethyl sulphate (1 eq) was added at once, and the reddish solution was stirred at room temperature for 20 h. The mixture was diluted with AcOEt and extracted four times with an aqueous solution of NaCl. Drying ($Na_2SO_4$) and removal of solvent gave (S)-1,3-dimethyl-7-nitro-5-phenyl-1H-benzo[e][1,4]diazepin-2(3H)-one as a yellow solid. Yield: 81%. M.p. 84-85° C.

[$^1H$]-NMR ($CDCl_3$): 1.76 (d, J=6.4 Hz, 3H, $CCH_3$); 3.49 (s, 3H, $NCH_3$); 3.71 (1, J=6.4 Hz, 1H, CHCO); 7.41-7.44 (m, 2H); 7.48-7.52 (m, 2H); 7.56-758 (m, 2H) (aromatic protons); 8.22 (d, J=2.8 Hz, H-6); 8.40 (dd, J=9.2, 2.8 Hz, H-8) ppm.

This compound (0.40 g, 1.30 mmol) was dissolved in 6N HCl (2.5 mL) and $SnCl_2.2H_2O$ (0.96 g, 3.3 eq) dissolved in 6N HCl (2.5 mL) was added. After stirring for 4 h at room temperature, the mixture was made alkaline with 10% NaOH and extracted with $CH_2Cl_2$. Drying ($Na_2SO_4$) and removal of solvent gave the title compound as a yellow solid: m.p. 219-221° C. Yield: 95%.

[$^1H$]-NMR ($CD_3OD$): 1.62 (d, J=6.4 Hz, 3H, CCH3); 3.37 (s, 3H, NCH3); 3.81 (q, J=6.4 Hz, 1H, CHMe); 6.51 (d, J=2.8 Hz, 1H, H-6); 6.97 (dd, J=8.8, 2.4 Hz, 1H, H-8); 7.28 (d, J=8.8 Hz, 1H, H-9); 7.39-7.43 (m, 2H, aromatic protons), 7.46-7.49 (m, 1H, aromati protonc), 7.53-7.57 (m, 2H, aromatic protons) ppm.

Example 2

(R)-7-amino-1,3-dimethyl-5-phenyl-1H-benzo[e][1,4]diazepin-2(3H)-one [(R)-1]

Following the same procedure used for the (S)-enantiomer, starting from (R)-Fmoc-alanine (Cruz, L. J.; Beteta, N G.; Eweson, A.; Albericio, F. *"One-Pot" Preparation of N-Carbamate Protected Amino Acids via the Azide. Organic Process Research & Development* 2004, 8, 920-924), (R)-7-amino-1,3-dimethyl-5-phenyl-1H-benzo[e][1,4]diazepin-2(3H)-one was obtained in 20% overall yield. Chemical and physical characteristics of the final and intermediate compounds are identical to those of their enantiomers.

Example 3

7-amino-1-methyl-5-phenyl-1H-benzo[e][1,4]diazepin-2(3H)-one (2)

This compound was prepared from Fmoc-glycine and 2-amino-4-nitro-benzophenone using the same procedure used for the enantiomers of 7-amino-1,3-dimethyl-5-phenyl-1H-benzo[e][1,4]diazepin-2(3H)-one. Chemical and physical characteristics of the intermediate and final compounds are reported:

7-nitro-5-phenyl-1H-benzo[e][1,4]diazepin-2(3H)-one: yellow solid, m.p. 226-227° C. [$^1H$]-NMR ($CD_3OD$): 4.31 (s, 2H, $CH_2$); 7.43 (d, J=9.2 Hz, 1H, H-9); 7.44-7.58 (m, 5H, Ph); 8.10 (d, J=2.8 Hz, 1H, H-6), 8.41 (dd, J=9.2, 2.8 Hz, 1H, H-8) ppm.

(1-methyl-7-nitro-5-phenyl-1H-benzo[e][1,4]diazepin-2(3H)-one: yellow solid, m.p. 69-70° C. [$^1H$]-NMR ($CDCl_3$): 3.48 (s, 3H, $NCH_3$); 3.78 (d, J=10.8 Hz, 1H, CHH); 4.94 (d, J=10.8 Hz, 1H, CHH); 7.42-7.46 (m, 2H, aromatic protons); 7.49-7.54 (m, 2H, aromatic protons); 7.58-760 (m, 2H, aromatic protons); 8.22 (d, J=2.4 Hz, H-6); 8.41 (dd, J=8.8, 2.4 Hz, H-8) ppm.

7-amino-1-methyl-5-phenyl-1H-benzo[e][1,4]diazepin-2(3H)-one: yellow solid, m.p. 236° C. [$^1H$]-NMR ($CDCl_3$): 3.36 (s, 3H, $NCH_3$); 3.86 (d, J=10.8 Hz, 1H, CHH); 4.54 (d, J=10.8 Hz, 1H, CHH); 6.50 (d, J=2.8 Hz, 1H, H-6); 6.97 (dd, J=8.8, 2.8 Hz, 1H, H-8); 7.29 (d, J=8.8 Hz, 1H, H-9); 7.40-7.44 (m, 2H, aromatic protons), 7.47-7.51 (m, 1H, aromatic protons), 7.55-7.57 (m, 2H, aromatic protons) ppm.

Example 4

(S)-ethyl 8-(1,3-dimethyl-2-oxo-5-phenyl-2,3-dihydro-1H-benzo[e][1,4]diazepin-7-ylamino)-8-oxooctanoate [(S)-3]

A mixture of (S)-1 (0.34 g, 1.22 mmol), ethyl hydrogensuberate (0.25 g, 1 eq), WSC (0.23 g, 1.20 eq) and HOBT (0.20 g, 1.20 eq) in ethanol-free $CHCl_3$ (20 mL) was stirred at room temperature for 3 days, then it was treated with 10% $NaHCO_3$ and the organic layer was separated. Drying ($Na_2SO_4$) and removal of the solvent gave a residue which was purified by flash chromatography ($CH_2Cl_2$/MeOH/$NH_4OH$ 99:1:0.1 as eluent). The title compound was obtained in 57% yield as a solid: m.p. 55-56° C.

[$^1H$]-NMR ($CDCl_3$): 1.23 (t, J=7.0 Hz, 3H, $OCH_2CH_3$); 1.27-1.38 (m, 4H, $2CH_2$); 1.54-1.72 (m, 4H, $2CH_2$); 1.71 (d, J=6.4 Hz, 3H, $CHCH_3$); 2.22-2.32 (m, 4H, $2CH_2$); 3.38 (s, 3H, $NCH_3$); 3.74 (q, J=6.4 Hz, 1H, CHMe); 4.08 (q, J=7.0 Hz, 2H, $OCH_2$); 7.24-7.44 (m, 5H, aromatic protons), 7.56-7.61 (m, 2H, aromatic protons), 7.79 (s, 1H, NH); 7.95 (dd, J=8.8, 2.0 Hz, 1H, H-8) ppm.

Example 5

(R)-ethyl 8-(1,3-dimethyl-2-oxo-5-phenyl-2,3-dihydro-1H-benzo[e][1,4]diazepin-7-ylamino)-8-oxooctanoate [(R)-3]

This compound was obtained in the same way as the (S)-enantiomer, starting from (R)-7-amino-1,3-dimethyl-5-phenyl-1H-benzo[e][1,4]diazepin-2(3H)-one. Overall yield: 66.5%. Chemical and physical characteristics are the same as the [(S)-3]enantiomer.

Example 6

Ethyl 8-(1-methyl-2-oxo-5-phenyl-2,3-dihydro-1H-benzo[e][1,4]diazepin-7-ylamino)-8-oxooctanoate (4)

This compound was prepared in the same way as compound [(S)-3], starting from compound 2, and it was obtained in 58% yield as a pale yellow solid, m.p. 50-51° C.

[¹H]-NMR (CDCl₃): 1.22 (t, J=7.0 Hz, 3H, OCH₂CH₃); 1.28-1.37 (m, 4H, 2CH₂); 1.53-1.70 (m, 4H, 2CH₂); 2.25 (t, J=7.6 Hz, 2H, CH₂); 2.30 (t, J=7.6 Hz, 2H, CH₂); 3.35 (s, 3H, NCH₃); 3.76 (d, J=11.2 Hz, 1H, CHH); 4.07 (q, J=7.0 Hz, 2H, OCH₂); 4.73 (d, J=11.2 Hz, 1H, CHH); 7.29 (d, J=8.8 Hz, 1H, H-9); 7.35-7.41 (m, 3H, aromatic protons), 7.41-7.46 (m, 1H, aromatic protons); 7.60-7.65 (m, 2H, aromatic protons); 7.98 (dd, J=8.8, 2.0 Hz, 1H, H-8); 8.09 (s, 1H, NH) ppm.

Example 7

(S)—N-1-(1,3-dimethyl-2-oxo-5-phenyl-2,3-dihydro-1H-benzo[e][1,4]diazepin-7-yl)-N8-hydroxyoctanediamide [(S)-5]

(S)-3 (0.30 g, 0.65 mmol) and NaOH (0.04 g, 1.5 eq) were stirred in a mixture of THF/MeOH/H₂O (1 mL each) for 2 h at room temperature. The mixture was treated with a saturated solution of NH₄Cl and extracted with AcOEt. Drying (Na₂SO₄) and removal of the solvent gave (S)-8-(1,3-dimethyl-2-oxo-5-phenyl-2,3-dihydro-1H-benzo[e][1,4]diazepin-7-ylamino)-8-oxooctanoic acid in 92% yield as a yellow solid. M.p. 87-88° C.

[¹H]-NMR (CD₃OD): 1.32-1.39 (m, 4H, 2CH₂); 1.55-1.68 (m, 7H, 2CH₂ and CCH₃); 2.25-2.33 (m, 4H, 2CH₂); 3.43 (s, 3H, NCH₃); 3.79 (q, J=6.4 Hz, 1H, CHMe); 7.40-7.57 (m, 7H, aromatic protons), 7.90 (dd, J=8.8, 2.4 Hz, 1H, H-8) ppm.

To a solution of the acid and Et₃N (1 eq) in CH₂Cl₂ (5 mL), BOP—Cl (1.1 eq), O-t-butyldimethylsilylhydroxylamine (1 eq) and Et₃N (3 eq) were added, and the mixture was stirred at room temperature for 20 h. The solvent was removed under vacuum, the residue was partitioned between H₂O and AcOEt, the organic layer was collected, dried (Na₂SO₄) and the solvent evaporated. The residue was dissolved in MeOH (10 mL) and heated at 50° C. for 20 h; then the solvent was removed leaving a residue which was purified by flash chromatography (CH₂Cl₂/MeOH/NH₄OH 99:1:0.1 as eluent). The title compound was obtained in 38% yield as a yellow solid. M.p. 135° C.

[¹H]-NMR (CD₃OD): 1.31-1.38 (m, 4H, 2CH₂); 1.56-1.68 (m, 7H, 2CH₂ and CCH₃); 2.07 (t, J=7.6 Hz, 2H, CH₂); 2.31 (m, J=7.6 Hz, 2H, CH₂); 3.43 (s, 3H, NCH₃); 3.79 (q, J=6.4 Hz, 1H, CHMe); 7.40-7.57 (m, 7H, aromatic protons), 7.90 (dd, J=8.8, 2.4 Hz, 1H, H-8) ppm.

Example 8

(R)—N1-(1,3-dimethyl-2-oxo-5-phenyl-2,3-dihydro-1H-benzo[e][1,4]diazepin-7-yl)-N8-hydroxyoctanediamide [(R)-5]

This compound was prepared as its (S)-enantiomer starting from (R)-ethyl 8-(1,3-dimethyl-2-oxo-5-phenyl-2,3-dihydro-1H-benzo[e][1,4]diazepin-7-ylamino)-8-oxooctanoate. Chemical and physical characteristics of the final and intermediate compounds are identical to those of their enantiomers.

Example 9

N1-(1-methyl-2-oxo-5-phenyl-2,3-dihydro-1H-benzo[e][1,4]diazepin-7-yl)-N8-hydroxyoctanediamide (6)

This compound was prepared in the same way as compound [(S)-5] starting from ethyl 8-(1-methyl-2-oxo-5-phenyl-2,3-dihydro-1H-benzo[e][1,4]diazepin-7-ylamino)-8-oxooctanoate (yield 45%). Chemical and physical characteristics of the intermediate and final compounds are reported:

8-(1-methyl-2-oxo-5-phenyl-2,3-dihydro-1H-benzo[e][1,4]diazepin-7-ylamino)-8-oxooctanoic acid (4): orange solid (m.p. 68-70° C.). [¹H]-NMR (CD₃OD): 1.32-1.41 (m, 4H, 2CH₂); 1.55-1.69 (m, 4H, 2CH₂); 2.26 (t, J=7.6 Hz, 2H, CH₂); 2.31 (t, J=7.6 Hz, 2H, CH₂); 3.42 (s, 3H, NCH₃); 3.86 (d, J=10.8 Hz, 1H, CHH); 4.61 (d, J=10.8 Hz, 1H, CHH); 7.41-7.57 (m, 7H, aromatic protons), 7.91 (dd, J=8.8, 2.4 Hz, 1H, H-8) ppm.

N1-(1-methyl-2-oxo-5-phenyl-2,3-dihydro-1H-benzo[e][1,4]diazepin-7-yl)-N8-hydroxy-octane diamide (6): yellow solid [m.p. 92° C. (d)]. [¹H]-NMR (CD₃OD): 1.30-1.40 (m, 4H, 2CH₂); 1.55-1.69 (m, 4H, 2CH₂); 2.07 (t, J=7.6 Hz, 2H, CH₂); 2.31 (t, J=7.6 Hz, 2H, CH₂); 3.42 (s, 3H, NCH₃); 3.86 (d, J=10.8 Hz, 1H, CHH); 4.61 (d, J=10.8 Hz, 1H, CHH); 7.41-7.58 (m, 7H, aromatic protons), 7.91 (dd, J=9.2, 2.4 Hz, 1H, H-8) ppm.

Example 10

(S)-7-iodo-1,3-dimethyl-5-phenyl-1H-benzo[e][1,4]diazepin-2(3H)-one [(S)-7]

(S)-1 (0.10 g, 0.36 mmol) was dissolved in conc. HCl (1 mL), the solution was diluted with H₂O (2 mL) and cooled to −15° C., then a solution of NaNO₂ (0.03 g, 1.2 eq) in H₂O (1 mL) was added dropwise. After 20 min stirring, a solution of KI (0.15 g, 2.5 eq) in H₂O (1 mL) was slowly dropped. The mixture was allowed to warm to room T and stirred for 1 h, then it was treated with Na₂CO₃ and extracted with Et₂O. The organic layer was washed first with a solution of Na₂SO₃ and then with H₂O, it was dried (Na₂SO₄) and evaporated, leaving a residue which was purified by flash chromatography (cyclohexane-ethyl acetate 7:3) giving the title compound in 39% yield as a white solid. M.p. 115° C.

[¹H]-NMR (CDCl₃): 1.73 (d, J=6.4 Hz, 3H, CCH₃); 3.40 (s, 3H, NCH₃); 3.71 (q, J=6.4 Hz, 1H, CHMe); 7.10 (d, J=8.8 Hz, 1H, H-9); 7.39-7.50 (m, 3H, aromatic protons); 7.57-7.63 (m, 3H, aromatic protons); 7.83 (dd, J=8.8, 2.0 Hz, 1H, H-8) ppm.

Example 11

(R)-7-iodo-1,3-dimethyl-5-phenyl-1H-benzo[e][1,4]diazepin-2(3H)-one [(R)-7]

This compound was prepared as its (S)-enantiomer starting from (R)-7-amino-1,3-dimethyl-5-phenyl-1H-benzo[e][1,4]diazepin-2(3H)-one [(R)-1]. Chemical and physical characteristics of this compound are identical to those of its (S)-enantiomer.

Example 12

7-iodo-1-methyl-5-phenyl-1H-benzo[e][1,4]diazepin-2(3H)-one (8)

This compound was prepared in the same way as (S)-7-iodo-1,3-dimethyl-5-phenyl-1H-benzo[e][1,4]diazepin-2(3H)-one (S)-7, starting from 7-amino-1-methyl-5-phenyl-1H-benzo[e][1,4]diazepin-2(3H)-one (2); it was obtained in 30% yield as a pale yellow solid (m.p. 86° C.).

[¹H]-NMR (CDCl₃): 3.38 (s, 3H, NCH₃); 3.77 (d, J=11.0 Hz, 1H, CHH); 4.85 (d, J=11.0 Hz, 1H, CHH); 7.11 (d, J=8.8 Hz, 1H, H-9); 7.40-7.46 (m, 2H, aromatic protons); 7.47-7.52

(m, 1H, aromatic proton); 7.60-7.64 (m, 3H, aromatic protons); 7.85 (dd, J=8.8, 2.0 Hz, 1H, H-8) ppm.

Example 13

(S)-6-(1,3-dimethyl-2-oxo-5-phenyl-2,3-dihydro-1H-benzo[e][1,4]diazepin-7-yl)hex-5-ynoic acid [(S)-9]

A mixture of (S)-7 (0.23 g, 0.33 mmol), 5-hexynoic acid (0.054 g, 1.5 eq), CuI (0.008 g, 0.12 eq), Pd(PPh$_3$)$_4$ (0.015 g, 0.04 eq) and Et$_3$N (1 mL) was stirred at room temperature for 17 h under N$_2$, then it was partitioned between a saturated solution of NH$_4$Cl and ethyl acetate. The organic phase was dried (Na$_2$SO$_4$), the solvent was removed under vacuum and the residue was purified by flash chromatography (CH$_2$Cl$_2$/MeOH 9:1) obtaining the title compound as a pale yellow solid: m.p. 62-63° C. (93% yield).

[$^1$H]-NMR (CDCl$_3$): 1.73 (d, J=6.4 Hz, 3H, CCH$_3$); 1.89 (quintet, J=7.2 Hz, 2H, CCH$_2$C); 2.46 (t, J=7.2 Hz, 2H, CH$_2$); 2.50 (t, J=7.2 Hz, 2H, CH$_2$); 3.42 (s, 3H, NCH$_3$); 3.72 (q, J=6.4 Hz, 1H, CHMe); 7.27 (d, J=8.8 Hz, 1H, H-9); 7.33 (d, J=2.0 Hz, 1H, H-6); 7.38-7.49 (m, 3H, aromatic protons); 7.55 (dd, J=8.8, 2.0 Hz, 1H, H-8); 7.58-7.62 (m, 2H, aromatic protons) ppm.

Example 14

(R)-6-(1,3-dimethyl-2-oxo-5-phenyl-2,3-dihydro-1H-benzo[e][1,4]diazepin-7-yl)hex-5-ynoic acid [(R)-9]

This compound was prepared as its (S)-enantiomer starting from (R)-7-iodo-1,3-dimethyl-5-phenyl-1H-benzo[e][1,4]diazepin-2(3H)-one [(R)-7]. Chemical and physical characteristics of this compound are identical to those of its (S)-enantiomer.

Example 15

6-(1-methyl-2-oxo-5-phenyl-2,3-dihydro-1H-benzo[e][1,4]diazepin-7-yl)hex-5-ynoic acid (10)

This compound was prepared in the same way as (S)-6-(1,3-dimethyl-2-oxo-5-phenyl-2,3-dihydro-1H-benzo[e][1,4]diazepin-7-yl)hex-5-ynoic acid [(S)-9] starting from 7-iodo-1-methyl-5-phenyl-1H-benzo[e][1,4]diazepin-2(3H)-one (8), and it was obtained in 69% yield as a pale yellow solid (m.p. 56° C.).

[$^1$H]-NMR (CDCl$_3$): 1.89 (quintet, J=7.2 Hz, 2H, CCH$_2$C); 2.46 (t, J=7.2 Hz, 2H, CH$_2$); 2.49 (t, J=7.2 Hz, 2H, CH$_2$); 3.41 (s, 3H, NCH$_3$); 3.77 (d, J=10.8 Hz, 1H, CHH); 4.84 (d, J=10.8 Hz, 1H, CHH); 7.28 (d, J=8.4 Hz, 1H, H-9); 7.32 (d, J=2.0 Hz, 1H, H-6); 7.40-7.46 (m, 3H, aromatic protons); 7.47-7.52 (m, 1H, aromatic proton); 7.57 (dd, J=8.4, 2.0 Hz, 1H, H-8); 7.60-7.65 (m, 2H, aromatic protons) ppm.

Example 16

(S)-6-(1,3-dimethyl-2-oxo-5-phenyl-2,3-dihydro-1H-benzo[e][1,4]diazepin-7-yl)-N-hydroxyhex-5-ynamide [(S)-11]

Following the same procedure used for (S)-5, starting from (S)-9 (0.13 g, 0.35 mmol), BOP—Cl (0.098 g, 1,1, eq), O-t-butyldimethylsilylhydroxylamine (0.051 g, 1 eq) and Et$_3$N (0.195 mL, 4 eq), the title compound was obtained in 24% yield as a white solid. M.p. 101-103° C.

[$^1$H]-NMR (CD$_3$OD): 1.64 (d, J=6.4 Hz, 3H, CCH$_3$); 1.85 (quintet, J=7.2 Hz, 2H, CCH$_2$C); 2.21 (t, J=7.2 Hz, 2H, CH$_2$); 2.42 (t, J=7.2 Hz, 2H, CH$_2$); 3.44 (s, 3H, NCH$_3$); 3.76 (q, J=6.4 Hz, 1H, CHMe); 7.22 (d, J=2.0 Hz, 1H, H-6); 7.42-7.48 (m, 2H, aromatic protons); 7.48-7.54 (m, 4H, aromatic protons): 7.64 (dd, J=8.8, 2.0 Hz, 1H, H-8) ppm.

Example 17

(R)-6-(1,3-dimethyl-2-oxo-5-phenyl-2,3-dihydro-1H-benzo[e][1,4]diazepin-7-yl)-N-hydroxyhex-5-ynamide [(R)-11]

This compound was prepared as its (S)-enantiomer starting from (R)-6-(1,3-dimethyl-2-oxo-5-phenyl-2,3-dihydro-1H-benzo[e][1,4]diazepin-7-yl)hex-5-ynoic acid (R)-9. Chemical and physical characteristics of this compound are identical to those of its (S)-enantiomer.

Example 18

6-(1-methyl-2-oxo-5-phenyl-2,3-dihydro-1H-benzo[e][1,4]diazepin-7-yl)-N-hydroxyhex-5-ynamide (12)

This compound was prepared in the same way as (S)-6-(1,3-dimethyl-2-oxo-5-phenyl-2,3-dihydro-1H-benzo[e][1,4]diazepin-7-yl)-N-hydroxyhex-5-ynamide (S-11) starting from 6-(1-methyl-2-oxo-5-phenyl-2,3-dihydro-1H-benzo[e][1,4]diazepin-7-yl)hex-5-ynoic acid (10), and it was obtained in 45% yield as a white solid (m.p. 86-87° C.).

[$^1$H]-NMR (CD$_3$OD): 1.85 (quintet, J=7.2 Hz, 2H, CCH$_2$C); 2.21 (t, J=7.2 Hz, 2H, CH$_2$); 2.42 (t, J=7.2 Hz, 2H, CH$_2$); 3.42 (s, 3H, NCH$_3$); 3.82 (d, J=10.8 Hz, 1H, CHH); 4.84 (d, J=10.8 Hz, 1H, CHH); 7.21 (d, J=2.0 Hz, 1H, H-6); 7.42-7.47 (m, 3H, aromatic protons); 7.49-7.55 (m, 4H, aromatic protons); 7.64 (dd, J=8.4, 2.0 Hz, 1H, H-8) ppm.

Example 19

3-amino-1-methyl-5-phenyl-1H-benzo[e][1,4]diazepin-2(3H)-one (14)

(Varnavas, A.; Rupena, P.; Lassiani, L.; Bocccù, E. *Synthesis of new benzodiazepine derivatives as potential cholecistokinin antagonists. Il Farmaco* 1991, 46, 391-401).

To a solution of benzyl 2-oxo-5-phenyl-2,3-dihydro-1H-benzo[e][1,4]diazepin-3-ylcarbamate (13) (Sherril R. G.; Sugg, E. E. *Improved Synthesis and Resolution of 3-Amino-1,3-dihydro-5-phenyl-2H-1,4-benzodiazepin-2-ones. J. Org. Chem.* 1995, 60, 730-734) (1.00 g, 2.60 mmol) in anhydrous DMF (10 mL), kept at 0° C. under N$_2$, NaH (60% dispersion in mineral oil, 0.10 g, 1 eq) was added in small portions. After 1.5 hr stirring at 0° C., methyl iodide (0.17 mL, 1.05 eq) was added at once; the mixture was stirred for additional 1.5 h at the same temperature, and then poured into a stirred solution of H$_2$O (60 mL) containing aqueous sodium hydrogen sulphate (2 mL, 1 N). A solid precipitated, which was filtered, dried under vacuum, and then purified by flash chromatography (CH$_2$Cl$_2$/MeOH/NH$_3$ 99:1:0.1 as eluent) giving benzyl 1-methyl-2-oxo-5-phenyl-2,3-dihydro-1H-benzo[e][1,4]diazepin-3-ylcarbamate in 91% yield. M.p. 78-80° C.

[$^1$H]-NMR (CDCl$_3$): 3.47 (s, 3H, Me); 5.13 (d, J=12.4 Hz, 1H, CHH); 5.17 (d, J=12.4 Hz, 1H, CHH); 5.33 (d, J=8.4 Hz, 1H, CH); 6.72 (d, J=8.4 Hz, 1H, NH); 7.22-7.28 (m, 1H), 7.28-7.42 (m, 9H), 7.44-7.50 (m, 1H) and 7.58-7.64 (m, 3H) (aromatic protons) ppm.

This compound (0.20 g, 0.50 mmol) was dissolved in 5.7 mL of HBr (33% solution in AcOH) under $N_2$ and the solution was kept stirring at room temperature for 2 hr, then diluted with $Et_2O$ (15 mL) to obtain a suspension. The mixture was filtered and the solid dissolved in $H_2O$. The aqueous solution was then made alkaline with $Na_2CO_3$ and extracted with AcOEt. The organic phase was dried ($Na_2SO_4$), the solvent was removed under vacuum obtaining the title compound in 99% yield. M.p. 62-64° C.

[$^1$H]-NMR ($CD_3OD$): 3.48 (s, 3H, Me); 4.43 (s, 1H, CH); 7.26-7.32 (m, 2H), 7.39-7.46 (m, 2H), 7.47-7.54 (m, 1H), 7.56-7.61 (m, 3H), 7.65-7.70 (m, 1H) (aromatic protons) ppm.

Example 20

Ethyl 8-(1-methyl-2-oxo-5-phenyl-2,3-dihydro-1H-benzo[e][1,4]diazepin-3-ylamino)-8-oxooctanoate (15)

Following the same procedure used for (S)-3, starting from 14, the title compound was obtained in 66% yield as a pale yellow solid (m.p. 138-140° C.).

[$^1$H]-NMR ($CDCl_3$): 1.25 (t, J=7.2 Hz, 3H, $CCH_3$); 1.31-1.45 (m, 4H, $2CH_2$); 1.60-1.75 (m, 4H, $2CH_2$); 2.29 (t, J=7.6 Hz, 2H, $CH_2$); 2.37 (td, J=7.6, 2.8 Hz, 2H, $CH_2$); 3.47 (s, 3H, $NCH_3$); 4.12 (q, J=7.2 Hz, 2H, $OCH_2$); 5.54 (d, J=8.4 Hz, 1H, CH); 7.23 (t, 1H, J=7.6 Hz, aromatic proton); 7.31 (d, J=8.0 Hz, 1H, aromatic proton); 7.33-7.41 (m, 4H, aromatic protons); 7.43-7.49 (m, 1H, aromatic proton); 7.56-7.61 (m, 3H, NH and aromatic protons) ppm.

Example 21

N1-hydroxy-N8-(1-methyl-2-oxo-5-phenyl-2,3-dihydro-1H-benzo[e][1,4]diazepin-3-yl)octanediamide (16)

15 (0.58 g, 1.29 mmol) and NaOH (0.08 g, 1.5 eq) were stirred in a mixture of $THF/MeOH/H_2O$ (2 mL each) for 2 h at room temperature. The mixture was treated with a saturated solution of $NH_4Cl$ and extracted with AcOEt. Drying ($Na_2SO_4$) and removal of the solvent gave 8-(1-methyl-2-oxo-5-phenyl-2,3-dihydro-1H-benzo[e][1,4]diazepin-3-ylamino)-8-oxooctanoic acid in 99% yield as a white solid (m.p. 140-141° C.).

[$^1$H]-NMR ($CDCl_3$): 1.37-1.44 (m, 4H, $2CH_2$); 1.63-1.75 (m, 4H, $2CH_2$); 2.34 (t, J=7.2 Hz, 2H, $CH_2$); 2.39 (td, J=7.6, 4.4 Hz, 2H, $CH_2$); 3.48 (s, 3H, $NCH_3$); 5.57 (d, J=8.0 Hz, 1H, CH); 7.24 (t, 1H, J=8.0 Hz, aromatic proton); 7.35 (dd, J=8.0, 1.2 Hz, 1H, aromatic proton); 7.37-7.42 (m, 3H, aromatic protons); 7.45-7.53 (m, 2H, aromatic protons); 7.57-7.63 (m, 3H, NH and aromatic protons) ppm.

To a solution of the acid and $Et_3N$ (1.3 eq) in anhydrous $CH_2Cl_2$ (5 mL), BOP—Cl (1.7 eq), dimethyl-t-butylhydroxylamine (1.5 eq) and $Et_3N$ (3 eq) were added, and the mixture was stirred at room temperature for 20 h. The solvent was removed under vacuum, the residue was partitioned between $H_2O$ and AcOEt, the organic layer was collected, dried ($Na_2SO_4$) and the solvent evaporated. The residue was dissolved in MeOH (10 mL) and heated at 50° C. for 20 h; then the solvent was removed leaving a residue which was purified by flash chromatography ($CH_2Cl_2/MeOH$ 95:5 as eluent). The title compound was obtained in 27% yield as a white solid m.p. 84-85° C.

[$^1$H]-NMR ($CD_3OD$): 1.33-1.48 (m, 4H, $2CH_2$); 1.58-1.73 (m, 4H, $2CH_2$); 2.10 (t, J=7.2 Hz, 2H, $CH_2$); 2.41 (t, J=7.6 Hz, 2H, $CH_2$); 3.48 (s, 3H, $NCH_3$); 5.39 (s, 1H, CH); 7.29-7.35 (m, 2H), 7.40-7.45 (m, 2H), 7.47-7.53 (m, 1H), 7.54-7.63 (m, 3H), and 7.66-7.73 (m, 1H) (aromatic protons) ppm.

Example 22

3-amino-5-phenyl-1,3-dihydro-benzo[e][1,4]diazepin-2-one (17)

Following the same procedure used for 14, starting from 13 (5.50 g, 14.28 mmol) the title compound was obtained as a white solid in 96% yield. M.p. 196-197° C.

[$^1$H]-NMR ($CD_3OD$): 4.41 (s, 1H, CH); 7.20-7.24 (m, 1H), 7.27-7.32 (m, 2H), 7.40-7.44 (m, 2H), 7.48-7.54 (m, 3H), 7.58-7.62 (m, 1H) (aromatic protons) ppm.

Example 23

(S)-1-phenyl-ethyl (2-oxo-5-phenyl-2,3-dihydro-1H-benzo[e][1,4]diazepinyl)carbamate [(3-S)-18] and (R)-1-phenyl-ethyl (2-oxo-5-phenyl-2,3-dihydro-1H-benzo[e][1,4]diazepinyl)carbamate [(3-R)-18]

(Sherril R. G.; Sugg, E. E. *Improved Synthesis and Resolution of 3-Amino-1,3-dihydro-5-phenyl-2H-1,4-benzodiazepin-2-ones. J. Org. Chem.* 1995, 60, 730-7342)

A solution of 17 (3.36 g, 13.38 mmol), 4-nitrophenyl (R)-1-phenylethyl carbonate (3.84 g, 1 eq) and triethylamine (1.86 ml, 1 eq) in anhydrous $CH_3CN$ (30 mL) was heated at 80° C. for 14 h. The solvent was evaporated and the residue partitioned between AcOEt and NaOH (10%). The organic phase was washed with brine, dried ($Na_2SO_4$) and the solvent evaporated to give a residue that was purified by flash chromatography (toluene/AcOEt 8:2 as eluent). The collected impure fractions again were separated in 7 chromatographic processes. The pure fractions of each diastereoisomer were collected to give (3-S)-18 (1.65 g, 31%, first eluting isomer) and (3-R)-18 (1.28 g, 24%, last eluting isomer) and a fraction containing both the isomers (0.79 g).

(3-S)-18: white solid, m.p. 108-109° C.

$[\alpha]^{20}_D$+25.2° (c=1, $CHCl_3$).

[$^1$H]-NMR (DMSO): 1.48 (d, J=6.8 Hz, 3H, $CHCH_3$); 5.01 (d, J=8.8 Hz, 1H, CHNH); 5.69 (q, J=6.8 Hz, 1H, $CHCH_3$); 7.13-7.54 (m, 13H), 7.60-7.64 (m, 1H) (aromatic protons); 8.33 (d, J=8.8 Hz, 1H, CHNH); 10.83 (s, 1H, NH) ppm.

(3-R)-18: white solid, m.p. 92-93° C.

$[\alpha]^{20}_D$+129.1° (c=1, $CHCl_3$).

[$^1$H]-NMR (DMSO): 1.48 (d, J=6.8 Hz, 3H, $CHCH_3$); 5.00 (d, J=8.8 Hz, 1H, CHNH); 5.70 (q, J=6.8 Hz, 1H, $CHCH_3$); 7.14-7.52 (m, 13H), 7.61-7.65 (m, 1H) (aromatic protons); 8.35 (d, J=8.8 Hz, 1H, CHNH); 10.85 (s, 1H, NH) ppm.

Example 24

(S)-1-phenyl-ethyl (1-methyl-2-oxo-5-phenyl-2,3-dihydro-1H-benzo[e][1,4]diazepin-3-il)carbamate [(3-S)-19] and (R)-1-phenyl-ethyl (1-methyl-2-oxo-5-phenyl-2,3-dihydro-1H-benzo[e][1,4]diazepin-3-il) carbamate [(3-R)-19]

(Sherril R. G.; Sugg, E. E. *Improved Synthesis and Resolution of 3-Amino-1,3-dihydro-5-phenyl-2H-1,4-benzodiazepin-2-ones. J. Org. Chem.* 1995, 60, 730-7342)

Following the same procedure used for 14, starting from (3-S)-18 and (3-R)-18 the diastereoisomers (3-S)-19 and (3-R)-19 were obtained in 95% and 97% yield respectively.

(3-S)-19:: white solid, m.p. 194-196° C.

[¹H]-NMR (CDCl₃): 1.60 (d, J=6.5 Hz, 3H, CHCH₃); 3.45 (s, 3H, NCH₃); 5.28 (d, J=8.4 Hz, 1H, CHNH); 5.77 (q, J=6.5 Hz, 1H, CHCH₃); 6.72 (d, J=8.4 Hz, 1H, CHNH); 7.18-7.66 (m, 14H, aromatic protons) ppm (3-R)-19:: white solid, m.p. 63° C.
[¹H]-NMR (CDCl₃): 1.56 (d, J=6.5 Hz, 3H, CHCH₃); 3.47 (s, 3H, NCH₃); 5.32 (d, J=8.8 Hz, 1H, CHNH); 5.79 (q, J=6.5 Hz, 1H, CHCH₃); 6.63 (d, J=8.8 Hz, 1H, CHNH); 7.16-7.60 (m, 14H, aromatic protons) ppm Example 25

(S)-Amino-1-methyl-5-phenyl-1H-benzo[e][1,4]diazepin-2(3H)-one [(S)-14] and (R)-amino-1-methyl-5-phenyl-1H-benzo[e][1,4]diazepin-2(3H)-one [(R)-14]

(Varnavas, A.; Rupena, P.; Lassiani, L.; Bocccù, E. *Synthesis of new benzodiazepine derivatives as potential cholecistokinin antagonists. Il Farmaco* 1991, 46, 391-401)

Following the same procedure used for 14, starting from (3-S)-19 and (3-R)-19 the enantiomers (3-S)-14 and (3-R)-14 were obtained in 79% and 74% yield respectively. Chemical and physical characteristics of the products are identical to those of 14.

(S)-14: $[\alpha]^{20}_D$ −170.6° (c=1, CH₃OH)
(R)-14: $[\alpha]^{20}_D$ +159.0° (c=1, CH₃OH)

Example 26

(S)-Ethyl 8-(1-methyl-2-oxo-5-phenyl-2,3-dihydro-1H-benzo[e][1,4]diazepin-3-ylamino)-8-oxooctanoate [(S)-15] and (S)-ethyl 8-(1-methyl-2-oxo-5-phenyl-2,3-dihydro-1H-benzo[e][1,4]diazepin-3-ylamino)-8-oxooctanoate [(R)-15]

Following the same procedure used for 15, starting from (3-S)-14 and (3-R)-14 the enantiomers (3-S)-15 and (3-R)-15 were obtained in 60% and 68% yield respectively. Chemical and physical characteristics of the products are identical to those of 15.

(S)-15: $[\alpha]^{20}_D$ −56.0° (c=1, CHCl₃)
(R)-15: $[\alpha]^{20}_D$ +55.3° (c=1, CHCl₃)

Example 27

(S)—N-1-hydroxy-N8-(1-methyl-2-oxo-5-phenyl-2,3-dihydro-1H-benzo[e][1,4]diazepin-3-yl)octanediamide [(S)-16] and (R)—N-1-hydroxy-N8-(1-methyl-2-oxo-5-phenyl-2,3-dihydro-1H-benzo[e][1,4]diazepin-3-yl)octanediamide [(R)-16]

Following the same procedure used for 16, starting from (3-S)-15 and (3-R)-15 the enantiomers (3-S)-16 and (3-R)-16 were obtained in 23% and 21% overall yield respectively. Chemical and physical characteristics of the products are identical to those of 16.

(S)-16: $[\alpha]^{20}_D$ −53.7° (c=1, CH₃OH)
(R)-16: $[\alpha]^{20}_D$ +45.4° (c=1, CH₃OH)

Pharmacological Activity

The new described compounds were tested for their ability to inhibit the histone deacetylase activity by western blot for the acetylated isoforms of histone H3 and H4 and also to induce growth arrest in cancer cells by activating apoptosis and/or cell differentiation. Initially, biological activities of newly synthesized HDACi were assessed by using the human acute promyelocytic leukemia cell line NB4, as the experimental model. Cells were maintained in RPMI (Bio-Whittaker Europe, Verviers, Belgio) supplemented with 10% of fetal calf serum (FCS, Boehringer Mannheim, Germania) and 2 mM glutamine (Merck, Darmstadt, Germania) at 37° C. in a humidified atmosphere of 5% CO₂. Cells were counted in a Burker chamber and cells viability was assessed by the trypan blu exclusion test.

Example 28

Leukemic blasts from either bone marrow biopsies or peripheral blood were collected from patients with acute myeloid leukemia, after giving informed consent. Leukemic blasts were purified by centrifugation at 1,700g on Lymphoprep (Europio, Les Ulis Cedex B, Francia), harvested under sterile conditions and cultured in RPMI medium supplemented with 10% of fetal calf serum and 2 mM glutamine at 37° C. in a humidified atmosphere containing 5% CO₂. The leukemia subtype was established according to the standard criteria of FAB classification (French-American-British; Bennett J M et al. *Proposed revised criteria for the classification of acute myeloid leukemia. A report of the French-American-British Cooperative Group. Ann Intern Med* 1985; 103:620-625).

Example 29

Histone Deacetylase Inhibition

Cells, obtained as described above, were harvested in sterile plates (Falcon, Becton Dickinson, Franklin Lakes, N.J.) at density of 6×10⁵/mL, and incubated for 6 hours with increasing drug concentration of single compounds. Then, the cells were lysated with RIPA buffer (50 mM Tris-HCl pH 7.4, 150 mM NaCl, 1% Nonidet P-40, 1 mM EDTA plus protease inhibitor cocktail (Protease Inhibitor Cocktail Set III, n° cat. 539134, Calbiochem, Merck, Darmstadt, Germany) and sonicated (Labsonic 1510) twice for 15s pulses at 1-2 Watts in ice. Protein concentration of cell extracts was determined according to the bicinchoninic acid colorimetric method (BCA, Pierce, Rockford, USA) by using serum bovine albumin as the standard (BSA, Sigma, Steinheim, Germania). Equal amounts of protein (20-40 µg/20-30 µL/well) were separated on NuPAGE Bis-Tris 12% gel (Novex, Invitrogen, Carlsbad, Calif.) 10% and transferred to nitrocellulose membranes (Pro-Bind, pore diameter=0.45 µm; Amersham Pharmacia). Then membranes, incubated in phosphate buffer saline (PBS) with 6% defatted dry milk as blocking solution to saturate unspecific binding sites, were probed overnight at 4° C. with primary antibodies (1;1000 dilution in PBS) raised against acetylated H4 a H3 histone isoforms (Upstate Technologies, Lake Placid, N.Y., USA). The immunoreactive proteins were revealed by the chemioluminescence method (ECL, Amersham Pharmacia Biotech) after membrane incubation with a suitable perossidate commercially available secondary antibody (anti-mouse/anti-rabbit/anti-goat IgG). The FIG. 1 panel A showed results of drug induced hyperacetylation of histone H3 and H4 isoforms. The experiment was performed with the compound (II) S form, where $R_1$ and $R_2$ can be independently a methyl group or hydrogen.

The densitometric values of blots were expressed in arbitrary units by using Gene Tools software and reported in Table 1.

TABLE 1

| Compound | Concentration | Acetyl-H3 | Acetyl-H4 |
|---|---|---|---|
| Untreated | — | 1 | 0 |
| DMSO | 0.0125% | 0.92 | 0 |
| Compound (II) racemic with $R_1$ or $R_2$ = Me | 1 μM | 3.73 | 1.67 |
|  | 2 μM | 4.61 | 5.92 |
|  | 5 μM | 5.19 | 16.29 |
| Compound (II) S form with $R_1$ or $R_2$ = Me | 0.5 μM | 2.88 | 1 |
|  | 1 μM | 3.85 | 1.33 |
|  | 2.5 μM | 5.23 | 12.96 |
| Compound (II) R form with $R_1$ or $R_2$ = Me | 0.5 μM | 2.5 | 0 |
|  | 1 μM | 2.54 | 0 |
|  | 2.5 μM | 3.69 | 0 |
| Compound (III) racemic with $R_1$ or $R_2$ = Me | 2 μM | 4.04 | 12.96 |
|  | 4 μM | 4.92 | 23.7 |
|  | 10 μM | 5.42 | 28.15 |
| Compound (III) S form with $R_1$ or $R_2$ = Me | 1 μM | 2.73 | 3 |
|  | 2 μM | 2.65 | 4.81 |
|  | 5 μM | 3.61 | 12.59 |
| Compound (III) R form with $R_1$ or $R_2$ = Me | 1 μM | 4.46 | 17.78 |
|  | 2 μM | 6.85 | 29.63 |
|  | 5 μM | 7.27 | 34.07 |
| Compound (II) with $R_1$ and $R_2$ = Me | 0.5 μM | 2.26 | 1.3 |
|  | 1 μM | 2.41 | 1.8 |
|  | 2.5 μM | 2.836 | 4 |
| Compound (III) with $R_1$ and $R_2$ = Me | 1 μM | 2.84 | 2.39 |
|  | 2 μM | 3.23 | 6.63 |
| Compound (IV) racemic | 0.5 μM | 2.67 | 1 |
|  | 1 μM | 3.17 | 5.78 |
|  | 2.5 μM | 3.38 | 10.89 |

Example 30

Evaluation of Cytostatic and Apoptotic Activity

Cells, were initially harvested at $4\times10^5$/mL (3 mL/well) cell density 24 well plate and incubated for 48 hours with increasing drug concentration. All compounds were solubilized in DMSO so that the final concentration of vehicle in culture was lower than 0.1%. At the end of treatment cell viability and apoptosis were evaluated by cytofluorimetric analysis using Anexin-V-Fluos staining (Annexin-V-FLUOS Staining Kit, Roche Molecular Biochemicals, Mannheim, Germany).

Necrotic cells, which are also Annexin-V positive, were identified by using Propidium iodide fluorochrome, that is capable of penetrating cell membranes of dying or dead cells and binding DNA.

Briefly, aliquots of cell suspensions (approximately $10^5$ cells) washed in buffer PBS, were resuspended in 5 μl of binding buffer containing annexin V-fluorescein isothiocyanate (FITC) and propidium iodide; incubation was carried out for 15 minutes at room temperature, and cells were then analyzed by flow cytometry (FACScan Becton-Dickinson, San Jose, Calif.).

The IC50 values (i.e. the drug concentration necessary to reduce cell density or viability by 50% as compared to untreated control cultures) obtained by graphic extrapolation of the Anexin-V results and expressed as percentage of viable cells over control were reported In Table 2.

TABLE 2

| Compound | IC50 (μM) |
|---|---|
| Compound (II) racemic $R_1$ or $R_2$ = Methyl | 3.4 |
| Compound (II) (S) form $R_1$ or $R_2$ = Methyl | 1.7 |
| Compound (II) (R) form $R_1$ or $R_2$ = Methyl | n.d. |
| Compound (III) racemic $R_1$ or $R_2$ = Methyl | 4 |
| Compound (III) (S) form $R_1$ or $R_2$ = Methyl | n.d. |
| Compound (III) (R) form $R_1$ or $R_2$ = Methyl | 3.7 |
| Compound (II) $R_1$ and $R_2$ = hydrogen | 4.9 |
| Compound (III) $R_1$ and $R_2$ = hydrogen | 3 |
| Compound (IV) racemic | 0.57 |

The FIG. 1 panel B shows results of the assay with Annexin-V-FLUOS Staining Kit in NB4 cell population treated with compound (II) S form, where $R_1$ and $R_2$ can be independently a methyl group or hydrogen. Data represent the percentage of viable cells as the function of drug concentration.

Example 31

Cells were fixed with acid acetic/methanol (⅓, v/v), then 20 μL of fixed cell suspension were placed on glass slide and let dry for 24 h. The cytosmears were stained with May-Grünwald-Giemsa and apoptotic cells were identified according to the typical morphologic parameters such as nuclear fragmentation, reduction of cell volume and apoptotic bodies. Image analyses were obtained by using a Nikon Eclipse 50i microscope equipped with a Nikon Digital Sight DS -5M (Nikon Corporation, Tokyo, Japan). The FIG. 1 panel C shows results of the experiment performed with the compound (II) S form, where $R_1$ and $R_2$ can be independently a methyl group or hydrogen. The images (magnification ×650) showed in treated cells a massive nuclear fragmentation suggestive of a typical apoptotic process.

Example 32

Evaluation of Differentiation Activity

The analysis of functional myeloid differentiation induced by compounds of the invention was accomplished by Nitro-Blu tetrazolium (NBT) reduction assay as described below. Cell suspension (approximately $10^5$/mL) were incubated in the presence of 0.25 mg/mL NBT and 500 ng of PMA (Phorbol-12-Myristate 13-acetate) (Sigma) at 37° C. for 30 minutes. Granulocyte or monocyte differentiated cell were capable of reducing NBT to dark formazan precipitate (blu positive cells). NBT positive cells were counted on Burker chamber and expressed as percentage of total cell population.

Identification of markers of myeloid maturation was determined by flow cytometry by labelling cells with PE-conjugated antibody and FITC-conjugated antibody to CD11b (granulocyte marker) and CD14 (monocyte marker) respectively (Becton-Dickinson). Cell suspension aliquots ($1\times10^5$ cells) were washed with cell wash buffer (Becton-Dickinson) and incubated with antibodies for 30 minutes in ice. After the incubation cells, resuspended in 0.3 mL of buffer containing Actinomycin D (Becton-Dickinson) to evaluate cell viability, were submitted to the cytofluorimetric analysis (FACScan, Becton-Dickinson). Cells incubated with appropriately labeled isotype controls were used to gate nonspecific fluorescence signal.

Example 33

Evaluation of Synergy between Compounds (II) and (III) and All-Trans Retinoic Acid (ATRA) Compound Compounds (II) in racemic form and enantiomers S or R.
Compounds (III) in racemic form and enantiomers S or R.
Compounds (II) with $R_1$ and $R_2$=hydrogen were tested for their capability to synergize with ATRA and for their ability to induce granulocyte differentiation in the human promyelocytic cell line NB4. ATRA at the final concentration of 1 µM is usually employed to induce granulocyte differentiation in NB4 cells.

NB4 cells were incubated for three days in presence of the compounds listed above, alone or in combination with ATRA. Granulocyte differentiation of leukemic cells was determined by (a) Nitro-Blu tetrazolium (NBT) reduction to dark formazan precipitate (blu positive cells) counting NBT positive cells on Burker chamber and (b) cytofluorimetric analysis of CD11b membrane expression (granulocyte marker, see example 32). Results were reported in Table 3, panels A, B and C.

Panel A: The combination of 3 µM of racemic compound (II) with low dose of ATRA (20 nM) was a much more effective inducer of differentiation than each of the agent given alone. This was shown by the substantial increase (up to 50-fold) of NBT positive cells and of CD11b positive cells in the treated populations. The same results was observed when 20 nM ATRA was combined to 1.5 µM S enantiomer. R enantiomer, alone or in combination with ATRA had no appreciable effect on granulocytic differentiation.

Panel B: The combination 3 µM of S enantiomer of compound (III) plus low dose of ATRA (20 nM) resulted in a strong synergistic increase of NBT positive cells while there was no increase in CD11b positive cells. R enantiomer alone (3 µM) augmented the percentage of CD11b positive cells while R enantiomer plus 20 nM ATRA led to an increase in the percentage of both CD11b and NBT positive NB4 cells which was comparable to that observed with 1 µM ATRA alone.

Panel C: 1.5 e 3 µM compound (II) led to a significant and dose-dependent increase in the amount of CD11b positive cells. A dose-dependent increase was also observed upon the addition of 20 nM ATRA in combination with the compound (II); the maximal synergistic effect was observed with the combination of 20 nM ATRA and 3 µM compound (II) that induced a percentage of NBT positive cells comparable to that obtained with 1 µM ATRA alone, and levels of CD11b expression which are greater than those observed with 1 µM ATRA administered alone and used as the positive control.

Taken together, these results indicate that the compound of the invention, even at low doses, potentiates strongly the cell differentiation activity of 20 nM ATRA.

Importantly, the compounds of the invention are the first hydroxamic HDACi reported so far to synergize with ATRA and enhance its differentiative effects in human acute promyelocytic leukemia cells NB4.

TABLE 3

| Cell line NB4 | Granulocytic differentiation | |
|---|---|---|
| | % of NBT+ cells | % of CD11b+ cells |
| Panel A | | |
| Compound (II) $R_1$ or $R_2$ = Methyl | | |
| Control | ≦1 | 11.2 |
| 20 nM ATRA | 12 | 13 |
| 1 µM ATRA | 78 | 80 |
| 3 µM Compound (II) racemic | ≦1 | 31.2 |
| 3 µM Compound (II) racemic + 20 nM ATRA | 72 | 81.7 |
| 1.5 µM Compound (II) (S) form | ≦1 | 36.3 |
| 1.5 µM Compound (II) (S) form + 20 nM ATRA | 41 | 62.3 |
| 1.5 µM Compound (II) (R) form | ≦1 | 14.2 |
| 1.5 µM Compound (II) (R) form + 20 nM ATRA | 13.1 | 19.8 |
| Panel B | | |
| Compound (III) $R_1$ or $R_2$ = Methyl | | |
| Control | 5 | 9.3 |
| 20 nM ATRA | 15 | 10 |
| 1 µM ATRA | 80 | 71.3 |
| 3 µM Compound (III) (S) form | 3 | 26 |
| 3 µM Compound (III) (S) form + 20 nM ATRA | 40 | 7.4 |
| 3 µM Compound (III) (R) form | 3 | 39.3 |
| 3 µM Compound (III) (R) form + 20 nM ATRA | 70 | 80 |
| Panel C | | |
| Compound (II) $R_1$ and $R_2$ = hydrogen | | |
| control | 5 | 9.9 |
| 20 nM ATRA | 15 | 10 |
| 1 µM ATRA | 80 | 72 |
| 1.5 µM Compound (II) | 2 | 44 |
| 1.5 µM Compound (II) + 20 nM ATRA | 45 | 74.3 |
| 3 µM Compound (II) | 3 | 69.3 |
| 3 µM Compound (II) + 20 nM ATRA | 80 | 94.7 |

Example 34

Ex Vivo Experimentation

The morphological effects induced by compound (II) were evaluated on human blasts from leukemic patients (ex vivo experimentation). Blasts were collected from either bone marrow biopsies or peripheral blood of patients with three different subtypes of acute myeloid leukemia (M1, M2 and M4), after giving informed consent. Blasts were purified by centrifugation at 1,700g on Lymphoprep (Europio, Les Ulis Cedex B, Francia), collected under sterile conditions and cultured in RPMI medium supplemented with 10% of fetal calf serum and 2 mM glutamine at 37° C. in a humidified atmosphere of 5% $CO_2$. The leukemia subtype was assessed by tusing he standard criteria of FAB classification (French-American-British; Bennett J M et al. *Proposed revised criteria for the classification of acute myeloid leukemia. A report of the French-American-British Cooperative Group*. Ann Intern Med 1985; 103:620-625).

Figure 2:
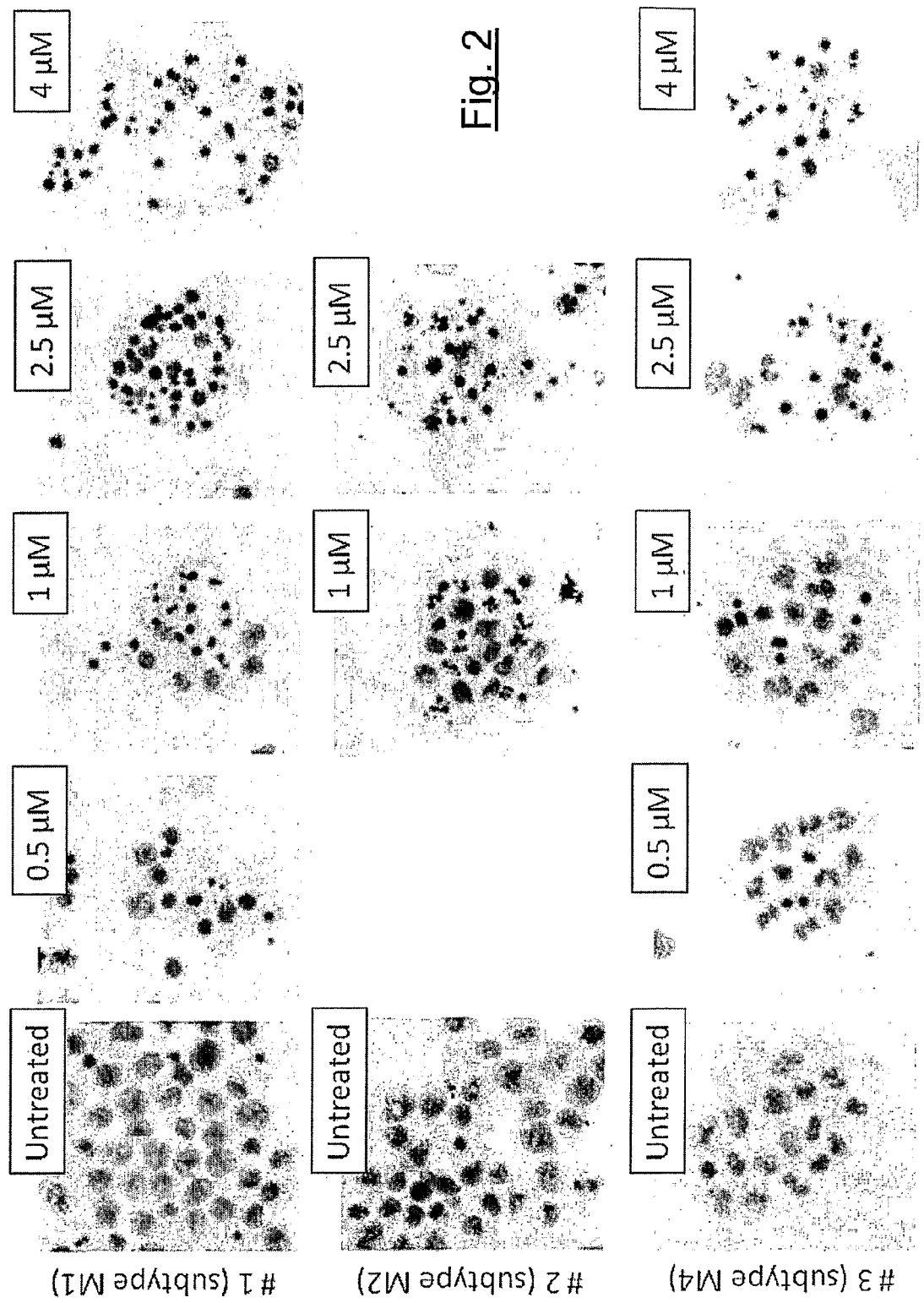
FIG. 2 shows the morphologic and apoptotic effects induced by the compound of FIG. 1 in blasts from patients affected by three distinct subtypes of acute myelogenous leukemia.

Leukemic blasts, incubated for 48 h with or without different concentrations of compound (II) S form, where $R_1$ and $R_2$ can be independently a methyl group or hydrogen, were fixed with a acid acetic/methanol solution (1/3, v/v), placed (20 µL of cell suspension) on a glass slide and let to dry for 24 h. The examination of cytosmears, once stained with May-Grünwald-Giemsa, showed that the invented compound (II) has the ability to induce apoptosis (apoptotic cells were identified according to the typical morphologic parameters such as nuclear fragmentation, reduction of cell volume and the presence of apoptotic bodies) in established leukemic cell line but also in primary cultures of blasts from leukemic patients. Image analyses (magnification: ×650) reported in FIG. 2, were obtained by using a Nikon Eclipse 50i microscope equipped with a Nikon Digital Sight DS -5M (Nikon Corporation, Tokyo, Japan).

The invention claimed is:

1. A compound of formula (I)

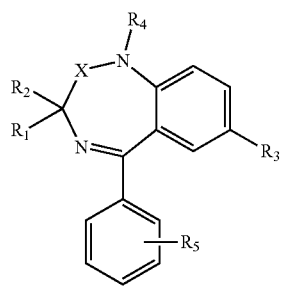

(I)

a pharmaceutically acceptable salt thereof or a pure (R) or (S) enantiomer thereof, wherein X is C=O or $CH_2$; $R_4$ is hydrogen or $C_1$-alkyl, and $R_1$, $R_2$, $R_3$, and $R_5$ are independently hydrogen, $(C_1-C_4)$-alkyl, halogen, $NO_2$, $(C_1-C_4)$ alkoxy, $(C_1-C_4)$alkylthio, amino, $(C_1-C_4)$dialkylamino or -A-CONHOH, with A selected from the group consisting of: $(C_1-C_8)$ alkylene, $(C_2-C_8)$alkenylene, $(C_2-C_8)$alkynylene, $(C_1-C_8)$ alkylene-NH—$CH_2$—, $(C_2-C_8)$alkenylene-NH—$CH_2$—, and $(C_0-C_8)$ alkylene-Y—$(C_1-C_8)$alkylene, and Y selected from the group consisting of —NHCO—, —O—, —NH—, and —S—;

provided that at least one of $R_1$, $R_2$, $R_3$, and $R_5$ is -A-CONHOH, and wherein when $R_3$ is -A-CONHOH, A is not $(C_1)$-$(C_3)$ alkylene or alkenylene.

2. The compound according to claim 1, the compound having a formula selected from formulas (II), (III) and (IV),

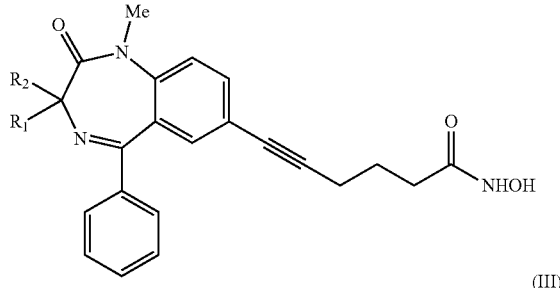

(II)

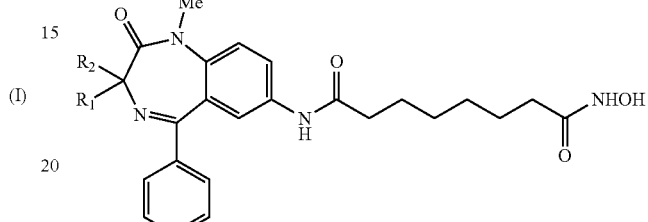

(III)

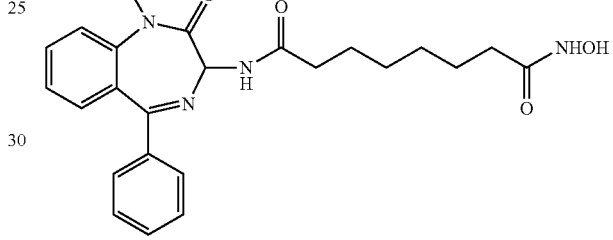

(IV)

a salt thereof or a pure (R) or (S) enantiomer thereof, wherein $R_1$, $R_2$ are independently hydrogen or methyl.

3. A pharmaceutical composition comprising at least one compound according to claim 1 as a chemiotherapeutic active principle and acceptable pharmaceutical excipients.

4. The pharmaceutical composition according to claim 3, wherein the composition is formulated for parenteral or oral administration.

5. The pharmaceutical composition according to claim 3, further comprising all-trans retinoic acid (ATRA).

6. A method for preparation of an antineoplastic pharmaceutical composition, the method comprising
combining the compound of claim 1 with pharmaceutically acceptable carriers and/or diluents.

7. A method of preparation of the compound according to claim 1, the method comprising performing the steps shown in scheme 1:

Scheme 1

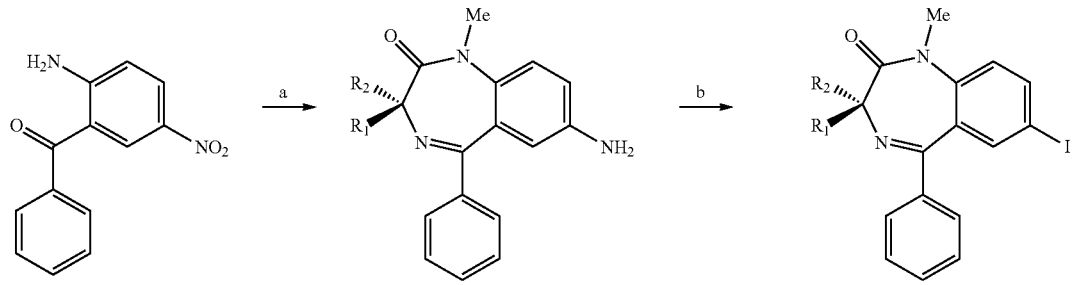

(S)-1: $R_1$ = Me, $R_2$ = H
(R)-1: $R_1$ = H, $R_2$ = Me
2: $R_1$, $R_2$ = H (S)-7: $R_1$ = Me, $R_2$ = H
(R)-7: $R_1$ = H, $R_2$ = Me
8: $R_1$, $R_2$ = H

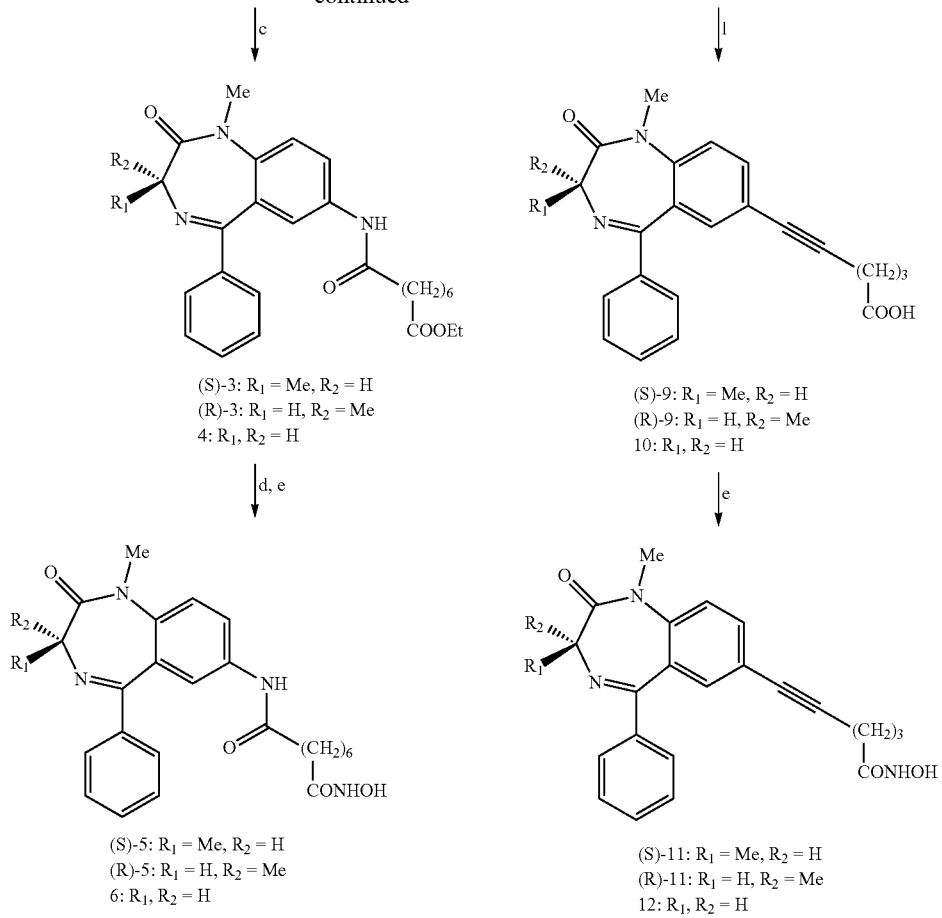

wherein:
a: i) (S) or (R)-Fmoc-alanine, or Fmoc-glicine, and $SOCl_2$;
   ii) $Et_3N$, $CH_2Cl_2$;
   iii $Me_2SO_4$, MeONa;
   iv $SnCl_2 \cdot H_2O$, HCl;
b: $NaNO_2$, KI;
c: ethyl hydrogensuberate, N—(3-dimethylaminopropyl)—N'-ethyl carbodiimide.HCl (WSC.HCl), 1-hydroxybenzotriazole (HOBT);
d: NaOH;
e: i) $TBDMSONH_2$, BOP-Cl;
   ii) MeOH; and
f: 5-hexynoic acid, CuI, $Pd(PPh_3)_4$, $Et_3N$.

8. A method for treatment in an individual of hematologic and solid malignancies selected from the group consisting of prostate cancer, breast cancer, hepatocellular liver carcinoma, colon cancer, melanoma, and acute myelogenous leukemia (AML), the method comprising
administering to the individual a therapeutically effective amount of the compound according to claim 1.

9. A method for treatment in an individual of hematologic and solid malignancies selected from the group consisting of prostate cancer, breast cancer, hepatocellular liver carcinoma, colon cancer, melanoma and acute myelogenous leukemia (AML), the method comprising
administering to the individual a therapeutically effective amount of the compound according to claim 2.

10. A pharmaceutical composition comprising at least one compound according to claim 2 as a chemiotherapeutic active principle and acceptable pharmaceutical excipients.

11. The pharmaceutical composition according to claim 10, wherein the composition is formulated for parenteral or oral administration.

12. The pharmaceutical composition according to claim 10, wherein the compound is in association with all-trans-retinoc acid (ATRA).

13. The compound according to claim 1, the compound being selected from the group consisting of:
(R) or (S)—N1-hydroxy-N8-(1-methyl-2-oxo-5-phenyl-2,3-dihydro-1H-benzo [e][1,4]diazepin-3-yl)octanediamide;
N1-(7-chloro-1-methyl-2-oxo-5-phenyl-2,3-dihydro-1H-benzo[e][1,4]diazepin-3-yl)-N8-hydroxyoctanediamide;
N1-hydroxy-N7-(1-methyl-2-oxo-5-phenyl-2,3-dihydro-1H-benzo[e][1,4]diazepin-3-yl) heptanediamide;
N1-hydroxy-N8-(1-methyl-2-oxo-5-phenyl-2,3-dihydro-7-nitro-1H-benzo [e][1,4]diazepin-3-yl)octanediamide;
N1-(7-chloro-5-(2-fluorophenyl)-2-oxo-2,3-dihydro-1H-benzo[e][1,4]diazepin-3-il)-N8-hydroxyoctanediamide;
(R) or (S)-N1-hydroxy-N8-(1,3-dimethyl-2-oxo-5-phenyl-2,3-dihydro-1H-1,4-benzo [e][1,4]diazepin-7-yl) octanediamide;
Ni -hydroxy-N8-(1,3-dimethyl-2-oxo-5-phenyl-2,3-dihydro-1H-1,4-benzo [e][1,4]diazepin-7-yl)-heptanediamide;
N1-hydroxy-N8-(1-methyl-2-oxo-3-ethyl-5-phenyl-2,3-dihydro-1H-1,4-benzo [e][1,4]diazepin-7-yl)-octanediamide;

N1-hydroxy-N8-(1-methyl-2-oxo-5-phenyl-2,3-dihydro-1H-1,4-benzo [e][1,4]diazepin-7-yl)-octanediamide;
(R) or (S)-N-hydroxy-6-(1,3-dimethyl-2-oxo-5-phenyl-2,3-dihydro-1H-benzo [e][1,4]diazepin-7-yl)-5-hexynamide;
N-hydroxy-7-(1,3-dimethyl-2-oxo-5-phenyl-2,3-dihydro-1H-benzo[e][1,4]diazepin-7-yl)-6-heptynamide;
N-hydroxy-6-(1-methyl-2-oxo-5-phenyl-2,3-dihydro-1H-benzo[e][1,4]diazepin-7-yl)-5-hexynamide;
N-hydroxy-6-[4-(1-methyl-2-oxo-2,3-dihydro-1H-benzo [e][1,4]diazepin-5-yl)-phenyl]-5-hexynamide;
N1-hydroxy-N8-[4-(1-methyl-2-oxo-2,3-dihydro-1H-benzo[e][1,4]diazepin-5-yl)-phenyl]-octanediamide;

N-hydroxy-5-(1-methyl-2-oxo-5-phenyl-2,3-dihydro-1H-benzo[e][1,4]diazepin-7-yl)-4-pentynamide;
N-hydroxy-7-(1-methyl-2-oxo-5-phenyl-2,3-dihydro-1H-benzo[e][1,4]diazepin-7-yl)-6-heptynamide;
N1-hydroxy-N6-(1-methyl-2-oxo-5-phenyl-2,3-dihydro-1H-benzo[e][1,4]diazepin-3-yl) hexanediamide;
N1-hydroxy-N9-(1-methyl-2-oxo-5-phenyl-2,3-dihydro-1H-benzo[e][1,4]diazepin-3-yl) nonanediamide.

14. A method of preparation of the compound according to claim 1, the method comprising performing the steps shown in scheme 2:

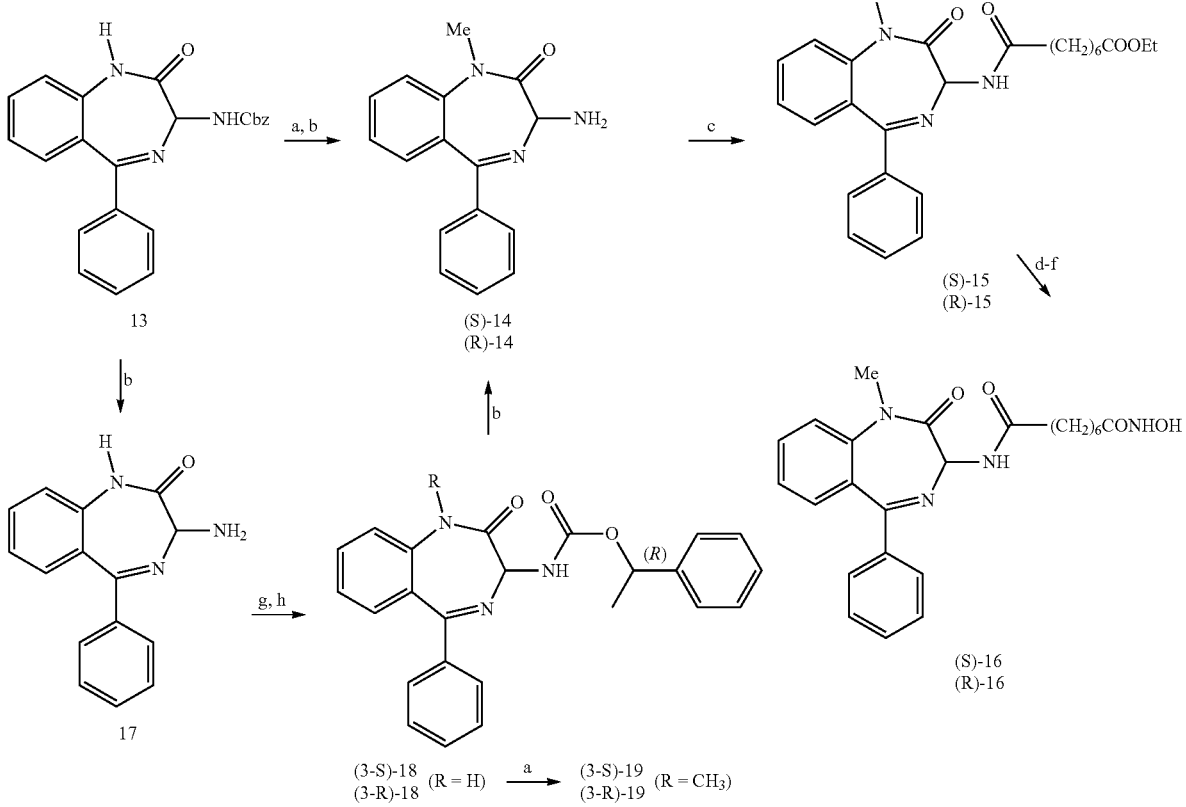

wherein:
a: NaH, CH₃I;
b: 33% HBr/AcOH;
c: ethyl hydrogensuberate, WSC, HOBT;
d: NaOH;
e: H₂NOSiMe₂tBu, BOP-Cl, Et₃N;
f: MeOH;
g: 4-nitrophenyl (R)-1-phenylethyl carbonate; and
h: separating diastereomers by chromatography.

* * * * *